United States Patent
Digan et al.

(10) Patent No.: US 6,423,512 B1
(45) Date of Patent: *Jul. 23, 2002

(54) FUSION POLYPEPTIDES

(75) Inventors: Mary Ellen Digan, Morristown; Philip Lake, Morris Plains, both of NJ (US); Hermann Gram, Weil am Rhein (AT)

(73) Assignee: Novartis AG, Basel (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/897,956

(22) Filed: Jul. 21, 1997

Related U.S. Application Data

(60) Provisional application No. 60/022,689, filed on Jul. 26, 1996.

(51) Int. Cl.[7] .................. A61K 38/17; C07K 14/705; C12N 15/62

(52) U.S. Cl. .................. 435/69.7; 435/243; 435/320.1; 435/325; 514/2; 514/8; 530/350; 530/363; 530/395; 530/868

(58) Field of Search .................. 530/363, 862, 530/868, 829, 350, 387.3, 866, 867, 395; 435/69.7, 325, 320.1, 243; 536/23.4, 23.5, 23.53; 514/2, 8; 424/134.1

(56) References Cited

U.S. PATENT DOCUMENTS 5,876,969 A   3/1999   Fleer et al. ................. 435/69.7

FOREIGN PATENT DOCUMENTS

| EP | 499112 | 8/1992 |
| WO | WO 89/05352 | 6/1989 |
| WO | WO 90/13653 | 11/1990 |

OTHER PUBLICATIONS

Nilsson, B. Curr.Opin. in Struc. Biol. 2:569–575, 1992.*

Sambrook, J et al. in Molecular Cloning: A Laboratory Manual: Second Edition. Sambrook, Fritsch and Maniatis, eds. Cold Spring Harbor Laboratory Press, Cold Spring Harbor, NY. pp. 1.11–1.20, 1989.*

R. Saban et al., J. Allergy Clin. Immunol., vol. 94, No. 5, pp. 836–843 (1994).

E.Scarselli et al., FEBS Letters, vol. 329, No. 1–2, pp. 223–226 (1993).

U. Blank et al., Nature, vol. 337, pp. 187–189, (1989).

* cited by examiner

*Primary Examiner*—David Saunders
(74) *Attorney, Agent, or Firm*—Diane E. Furman; Gregory D. Ferraro

(57) ABSTRACT

Fusion polypeptides and salts thereof comprising at least one IgE-binding domain fused to at least one human serum albumin component, optionally via a peptide linker, and in particular, dimeric fusion polypeptides comprising HSA protein fused, at each of its amino and carboxy termini, to an extracellular domain of the α-chain of the human high affinity receptor for IgE (FcεRIα); process for the preparation thereof, functionally equivalent polypeptides which are intermediates in their preparation, and polynucleotide and oligonucleotide intermediates and vectors therefor. They are indicated for use in the prevention and/or treatment of IgE-mediated allergic diseases and related disorders such as atopic dermatitis, atopic asthma and chronic urticaria.

13 Claims, 21 Drawing Sheets

SCHEMATIC REPRESENTATION OF THREE FUSION POLYPEPTIDES
I. MONOMERS:
1. HSA-IgE$^R$    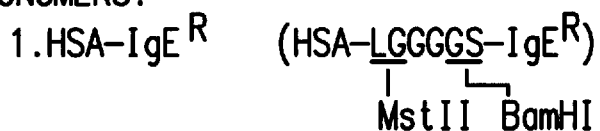
2. IgE$^R$-HSA    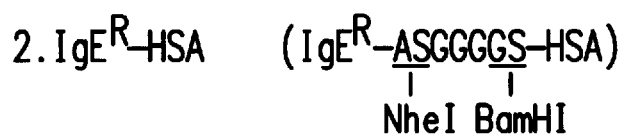
I. DIMERS:
1. IgE$^R$-HSA-IgE$^R$    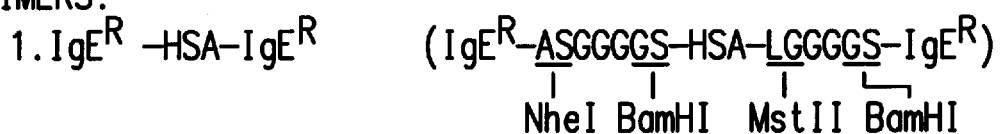
FIG.3

PCR PRIMERS
IgE RECEPTOR cDNA
A. HSA-LEADING:
B. IgER-LEADING
C. IgER-ALONE
FIG.4

HSA SEQUENCING OLIGONUCLEOTIDES

HSA sequencing oligos:

1    s/n459031-sequencing oligo for HSA @ ~200bp-coding strand
5'TCAAAGCCTTGGTGTTGATTG3'

2    s/n458896-sequencing oligo for HSA @ ~400bp-coding strand
5'TGAAATGGCTGACTGCTGTG3'

3    s/n458858-sequencing oligo for HSA @ ~600bp-coding strand
5'AGGTATAAAGCTGCTTTTACAG3'

4    s/n450959-sequencing oligo for HSA @ ~800bp-coding strand
5'TGAGCCAGAGATTTCCCAAAG3'

5    s/n451995-sequencing oligo for HSA @ ~1000bp-coding strand
5'TCCCACTGCATTGCCGAAGTG3'

6    s/n485788-sequencing oligo for HSA @ ~1200bp-coding strand
5'CTAGAGAAGTGCTGTGCCGCT3'

7    s/n480661-sequencing oligo for HSA @ ~1400bp-coding strand
5'TGTCAACTCCAACTCTTGT3'

8    s/n451389-sequencing oligo for HSA @ ~1600bp-coding strand
5'CAGCTCTGGAAGTCGATGAAA3'

9    s/n462782-sequencing oligo for HSA @ ~780bp-noncoding strand
5'CTTTGAAAGCTCTTTCTCCA3'

10    s/n437503-sequencing oligo for HSA @ ~1335bp-noncoding strand
5'ATTCTGGAATTTGTACTCTCC3'

12    s/n434978-sequencing oligo near 5' end of HSA for sequencing linkers-noncoding strand
5'ACACTGCTGAAGATACTGAGC3'

16    s/n465147-sequencing oligo for HSA @ ~550bp-noncoding strand
5'TCTGGCAATTTCATATAAGTA3'

17    s/n428935-sequencing oligo for HSA @ ~1455bp-coding strand
5'ATGTTGTAAACATCCTGAAGC3'

22    s/n466444-sequencing oligo near 3' end of HSA for sequencing linkers-coding strand
5'ACCTGCTTTGCCGAGGAGGGT3'

30    Sequencing oligo for HSA @ ~150bp-coding strand
5'ACAAGAGTGAGGTTGCTCATC3'

FIG.6

IgE$^R$ SEQUENCING OLIGONUCLEOTIDES

11  s/n479818-sequencing oligo near 5' end of IgE$^R$ for sequencing linkers-noncoding strand
5'CCTTTAAATATTCTATTCCAT3'

13  s/n486284-sequencing oligo for IgE$^R$ @ 220bp-coding strand
5'GAAGTCAGTTCCACCAAATGGT3'

23  s/n418915-sequencing oligo for IgE$^R$ @ 420bp-coding strand
5'GATGGAGGGCCAGCCCCTCTT3'

FIG.7

MUTAGENIC OLIGONUCLEOTIDES FOR HSA

14 s/n450055-mutagenic oligo for HSA to change E back to K-positive
    5'TGTGAGCTTTTTAAGCAGCTTGGAG3'

15 s/n464834-mutagenic oligo for HSA to change E back to K-negative control for complementary strand
    5'CTCCAAGCTGCTTAAAAAGCTCACA3'

FIG.8A

PCR AND LINKER OLIGONUCLEOTIDES

18 s/n407231-PCR oligo for IgE$^R$ for HSA-IgE$^R$ construct at 5' end adding a BamHI site for cloning-coding strand
    5'TCAT<u>GGATCC</u>GTCCCTCAGAAACCTAAGGTCTCCTTGAAC3'
         BamHI

19 s/n481113-PCR oligo for IgE$^R$ for HSA-IgE$^R$ construct at 3' end extacellular domain adding stop, EcoRI and SalI-non-coding strand
    5'TCAT<u>GTCGAC</u> <u>GAATTC</u> TTACTATAGCCAGTACTTCTCACGCGGAGC
         SalI    EcoRI  *  *
    TTTTAT3'

20 s/n432172-PCR oligo for IgE$^R$ for IgE$^R$-HSA construct at 5' end adding SstI, EcoRI, and Kozak-coding strand
    5'TCAT <u>GAGCTC</u> <u>GAATTC</u> <u>ACC</u>ATGGCTCCTGCCATGGAATCCCCTACT
          SstI    EcoRI   Kozak
    CTA3'

24 s/n489617-PCR oligo for HSA for HSA-IgE$^R$ construct at 5' end adding SpeI,EcoRI and Kozak-coding strand
    5'TCAT <u>ACTAGT</u> <u>GAATTC</u> <u>ACC</u> ATGAAGTGGGTAACCTTTATTTCCCTT
          SpeI    EcoRI   Kozak
    CTT3'

25 s/n412766-PCR oligo for HSA for HSA-IgE$^R$ construct at 3' end adding stop,EcoRI and HindIII-non-coding strand
    5'TCAT <u>AAGCTT</u> <u>GAATTC</u> CTATTATAAGCCTAAGGCAGCTTGACTTGC
          HindIII EcoRI  *   *   MstII
    AGC3'

FIG.8B

26 PCR oligo for HSA for IgE$^R$-HSA construct at 5' end adding NotI,NheI, linker,and BamHI-coding strand 5'<u>GCGGCCGC</u> <u>GCTAGC</u>GGTGGAGGTGGA<u>TCCGATGCAC</u>
          <u>NotI</u>     <u>NheI</u>              BamHI
        ACAAGAGTGAGGTTGCTCATCGGTTT3'

27 PCR oligo for HSA for IgE$^R$-HSA construct at NcoI site of HSA-non-coding strand 5'TCAT<u>CCATGG</u>CAGCATTCCGTGTGGACTTTGGTAAGA3'
             NcoI

28 Linker oligo for HSA-IgE$^R$ construct to be ligated as a MstII.HindIII fragment-coding strand 5'<u>TTAGG</u>TGGAGGTGGA<u>TCCA</u>3'
          <u>MstII</u>       BamHI

29 Linker oligo for HSA-IgE$^R$ construct to be ligated as a MstII,HindIII fragment-non-coding strand 5'<u>AGCTT</u> <u>GGATCC</u>ACCTCCACC3'
          HindIII BamHI

31 PCR oligo for IgE$^R$ for IgE$^R$-HSA construct at 3' end of extracellular domain adding NotI and NheI-deletes a second NheI site-non-coding strand 5'TCAT<u>GCGGCCGC</u> <u>GCTAGC</u>AAGCCAGTACTTCTCACGCGGAGCTTT
             <u>NotI</u>       <u>NheI</u>
        A3'

FIG.8C

NUCLEOTIDE AND AMINO ACID SEQUENCE OF HSA

```
ATGAAGTGGGTAACCTTTATTTCCCTTCTTTTTCTCTTTAGCTCGGCTTATTCCAGGGGT
 M  K  W  V  T  F  I  S  L  L  F  L  F  S  S  A  Y  S  R  G

GTGTTTCGTCGAGATGCACACAAGAGTGAGGTTGCTCATCGGTTTAAAGATTTGGGAGAA
 V  F  R  R  D  A  H  K  S  E  V  A  H  R  F  K  D  L  G  E
   GAAAATTTCAAAGCCTTGGTGTTGATTGCCTTTGCTCAGTATCTTCAGCAGTGTCCATTT
    E  N  F  K  A  L  V  L  I  A  F  A  Q  Y  L  Q  Q  C  P  F
   GAAGATCATGTAAAATTAGTGAATGAAGTAACTGAATTTGCAAAAACATGTGTAGCTGAT
    E  D  H  V  K  L  V  N  E  V  T  E  F  A  K  T  C  V  A  D
   GAGTCAGCTGAAAATTGTGACAAATCACTTCATACCCTTTTTGGAGACAAATTATGCACA
    E  S  A  E  N  C  D  K  S  L  H  T  L  F  G  D  K  L  C  T
    GTTGCAACTCTTCGTGAAACCTATGGTGAAATGGCTGACTGCTGTGCAAAACAAGAACCT
     V  A  T  L  R  E  T  Y  G  E  M  A  D  C  C  A  K  Q  E  P
   GAGAGAAATGAATGCTTCTTGCAACACAAAGATGACAACCCAAACCTCCCCCGATTGGTG
    E  R  N  E  C  F  L  Q  H  K  D  D  N  P  N  L  P  R  L  V
   AGACCAGAGGTTGATGTGATGTGCACTGCTTTTCATGACAATGAAGAGACATTTTTGAAA
    R  P  E  V  D  V  M  C  T  A  F  H  D  N  E  E  T  F  L  K
   AAATACTTATATGAAATTGCCAGAAGACATCCTTACTTTTATGCCCCGGAACTCCTTTTC
    K  Y  L  Y  F  I  A  R  R  H  P  Y  F  Y  A  P  E  L  L  F
   TTTGCTAAAAGGTATAAAGCTGCTTTTACAGAATGTTGCCAAGCTGCTGATAAAGCTGCC
    F  A  K  R  Y  K  A  A  F  T  E  C  C  Q  A  A  D  K  A  A
   TGCCTGTTGCCAAAGCTCGATGAACTTCGGGATGAAGGGAAGGCTTCGTCTGCCAAACAG
    C  L  L  P  K  L  D  E  L  R  D  E  G  K  A  S  S  A  K  Q
   AGACTCAAATGTGCCAGTCTCCAAAAATTTGGAGAAAGAGCTTTCAAAGCATGGGCAGTG
    R  L  K  C  A  S  L  Q  K  F  G  E  R  A  F  K  A  W  A  V
   GCTCGCCTGAGCCAGAGATTTCCCAAAGCTGAGTTTGCAGAAGTTTCCAAGTTAGTGACA
    A  R  L  S  Q  R  F  P  K  A  E  F  A  E  V  S  K  L  V  T
   GATCTTACCAAAGTCCACACGGAATGCTGCCATGGAGATCTGCTTGAATGTGCTGATGAC
    D  L  T  K  V  H  T  E  C  C  H  G  D  L  L  E  C  A  D  D
   AGGGCCGACCTTGCCAAGTATATCTGTGAAAATCAGGATTCGATCTCCAGTAAACTGAAG
    R  A  D  L  A  K  Y  I  C  E  N  Q  D  S  I  S  S  K  L  K
   GAATGCTGTGAAAAACCTCTGTTGGAAAAAATCCCACTGCATTGCCGAAGTGGAAAATGAT
    E  C  C  E  K  P  L  L  E  K  S  H  C  I  A  E  V  E  N  D
   GAGATGCCTGCTGACTTGCCTTCATTAGCTGCTGATTTTGTTGAAAGTAAGGATGTTTGC
    E  M  P  A  D  L  P  S  L  A  A  D  F  V  E  S  K  D  V  C
   AAAAACTATGCTGAGGCAAAGCATGTCTTCCTGGGCATGTTTTTGTATGAATATGCAAGA
    K  N  Y  A  E  A  K  D  V  F  L  G  M  F  L  Y  E  Y  A  R
```

FIG.12A

```
    AGGCATCCTGATTACTCTGTCGTGCTGCTGCTGAGACTTGCCAAGACATATGAAACCACT
R H P D Y S V V L L L R L A K T Y E T T
    CTAGAGAAGTGCTGTGCCGCTGCAGATCCTCATGAATGCTATGCCAAAGTGTTCGATGAA
L E K C C A A A D P H E C Y A K V F D F
    TTTAAACCTCTTGTGGAAGAGCCTCAGAATTTAATCAAACAAAACTGTGAGCTTTTTAAG
F K P L V E E P Q N L I K Q N C E L F K
    CAGCTTGGAGAGTACAAATTCCAGAATGCGCTATTAGTTCGTTACACCAAGAAAGTACCC
Q L G E Y K F Q N A L L V R Y T K K V P
    CAAGTGTCAACTCCAACTCTTGTAGAGGTCTCAAGAAACCTAGGAAAAGTGGGCAGCAAA
Q V S T P T L V E V S R N L G K V G S K
    TGTTGTAAACATCCTGAAGCAAAAAGAATGCCCTGTGCAGAAGACTATCTATCCGTGGTC
C C K H P E A K R M P C A E D Y L S V V
    CTGAACCAGTTATGTGTGTTGCATGAGAAAACGCCAGTAAGTGACAGAGTCACAAAATGC

L N Q L C V L H E K T P V S D R V T K C
    TGCACAGAGTCCTTGGTGAACAGGCGACCATGCTTTTCAGCTCTGGAAGTCGATGAAACA
C T E S L V N R R P C F S A L E V D E T
    TACGTTCCCAAAGAGTTTAATGCTGAAACATTCACCTTCCATGCAGATATATGCACACTT
Y V P K E F N A E T F T F H A D I C T L
    TCTGAGAAGGAGAGACAAATCAAGAAACAAACTGCACTTGTTGAGCTTGTGAAACACAAG
S E K E R Q I K K Q T A L V E L V K H K
    CCCAAGGCAACAAAAGAGCAACTGAAAGCTGTTATGGATGATTTCGCAGCTTTTGTAGAG
P K A T K E Q L K A V M D D F A A F V E

AAGTGCTGCAAGGCTGACGATAAGGAGACCTGCTTTGCCGAGGAGGGTAAAAAACTTGTT
K C C K A D D K E T C F A E E G K K L V

GCTGCAAGTCAAGCTGCCTTAGGCTTA
A A S Q A A L G L
```

FIG.12B

NUCLEOTIDE AND AMINO ACID SEQUENCE OF IgE$^R$

ATGGCTCCTGCCATGGAATCCCCTACTCTACTGTGTGTAGCCTTACTGTTCTTCGCTCCA
M A P A M E S P T L L C V A L L F F A P -
GATGGCGTGTTAGCAGTCCCTCAGAAACCTAAGGTCTCCTTGAACCCTCCATGGAATAGA
D G V L A V P Q K P K V S L N P P W N R -
ATATTTAAAGGAGAGAATGTGACTCTTACATGTAATGGGAACAATTTCTTTGAAGTCAGT
I F K G E N V T L T C N G N N F F E V S -
TCCACCAAATGGTTCCACAATGGCAGCCTTTCAGAAGAGACAAATTCAAGTTTGAATATT
S T K W F H N G S L S E E T N S S L N I -
GTGAATGCCAAATTTGAAGACAGTGGAGAATACAAATGTCAGCACCAACAAGTTAATGAG
V N A K F E D S G E Y K C Q H Q Q V N E -
AGTGAACCTGTGTACCTGGAAGTCTTCAGTGACTGGCTGCTCCTTCAGGCCTCTGCTGAG
S E P V Y L E V F S D W L L L Q A S A E

GTGGTGATGGAGGGCCAGCCCCTCTTCCTCAGGTGCCATGGTTGGAGGAACTGGGATGTG
V V M E G Q P L F L R C H G W R N W D V
TACAAGGTGATCTATTATAAGGATGGTGAAGCTCTCAAGTACTGGTATGAGAACCACAAC
Y K V I Y Y K D G E A L K Y W Y E N H N
ATCTCCATTACAAATGCCACAGTTGAAGACAGTGGAACCTACTACTGTACGGGCAAAGTG
I S I T N A T V E D S G T Y Y C T G K V
TGGCAGCTGGACTATGAGTCTGAGCCCCTCAACATTACTGTAATAAAAGCTCCGCGTGAG
W Q L D Y E S E P L N I T V I K A P R E
AAGTACTGGCTACAATTTTTTATCCCATTGTTGGTGGTGATTCTGTTTGCTGTGGACACA
K Y W L Q F F I P L L V V I L F A V D T
GGATTATTTATCTCAACTCAGCAGCAGGTCACATTTCTCTTGAAGATTAAGAGAACCAGG
G L F I S T Q Q Q V T F L L K I K R T R

AAAGGCTTCAGACTTCTGAACCCACATCCTAAGCCAAACCCCAAAAACAACTG
K G F R L L N P H P K P N P K N N

FIG.13

NUCLEOTIDE AND AMINO ACID AMINO ACID SEQUENCE OF THE EcoRI fragment of R-H-R/SK#50

```
GAATTCACCATGGCTCCTGCCATGGAATCCCCTACTCTACTGTGTGTAGCCTTACTGTTC
     M  A  P  A  M  E  S  P  T  L  L  C  V  A  L  L  F
      TTCGCTCCAGATGGCGTGTTAGCAGTCCCTCAGAAACCTAAGGTCTCCTTGAACCCTCCA
    F  A  P  D  G  V  L  A  V  P  Q  K  P  K  V  S  L  N  P  P
        TGGAATAGAATATTTAAAGGAGAGAATGTGACTCTTACATGTAATGGGAACAATTTCTTT
     W  N  R  I  F  K  G  E  N  V  T  L  T  C  N  G  N  N  F  F
         GAAGTCAGTTCCACCAAATGGTTCCACAATGGCAGCCTTTCAGAAGAGACAAATTCAAGT
    E  V  S  S  T  K  W  F  H  N  G  S  L  S  E  E  T  N  S  S
          TTGAATATTGTGAATGCCAAATTTGAAGACAGTGGAGAATACAAATGTCAGCACCAACAA
    L  N  I  V  N  A  K  F  E  D  S  G  E  Y  K  C  Q  H  Q  Q
           GTTAATGAGAGTGAACCTGTGTACCTGGAAGTCTTCAGTGACTGGCTGCTCCTTCAGGCC
    V  N  E  S  E  P  V  Y  L  E  V  F  S  D  W  L  L  L  Q  A

TCTGCTGAGGTGGTGATGGAGGGCCAGCCCCTCTTCCTCAGGTGCCATGGTTGGAGGAAC
 S  A  E  V  V  M  E  G  Q  P  L  F  L  R  C  H  G  W  R  N
         TGGGATGTGTACAAGGTGATCTATTATAAGGATGGTGAAGCTCTCAAGTACTGGTATGAG
    W  D  V  Y  K  V  I  Y  Y  K  D  G  E  A  L  K  Y  W  Y  E
          AACCACAACATCTCCATTACAAATGCCACAGTTGAAGACAGTGGAACCTACTACTGTACG
    N  H  N  I  S  I  T  N  A  T  V  E  D  S  G  T  Y  Y  C  T
           GGCAAAGTGTGGCAGCTGGACTATGAGTCTGAGCCCCTCAACATTACTGTAATAAAAGCT
    G  K  V  W  Q  L  D  Y  E  S  E  P  L  N  I  T  V  I  K  A
            CCGCGTGAGAAGTACTGGCTTgctagcggtggaggtggatccGATGCACACAAGAGTGAG
    P  R  E  K  Y  W  L  A  S  G  G  G  G  S  D  A  H  K  S  E
             GTTGCTCATCGGTTTAAAGATTTGGGAGAAGAAAATTTCAAAGCCTTGGTGTTGATTGCC
    V  A  H  R  F  K  D  L  G  E  E  N  F  K  A  L  V  L  I  A
              TTTGCTCAGTATCTTCAGCAGTGTCCATTTGAAGATCATGTAAAATTAGTGAATGAAGTA
    F  A  Q  Y  L  Q  Q  C  P  F  E  D  H  V  K  L  V  N  E  V
               ACTGAATTTGCAAAAACATGTGTTGCTGATGAGTCAGCTGAAAATTGTGACAAATCACTT
    T  E  F  A  K  T  C  V  A  D  E  S  A  E  N  C  D  K  S  L
```

FIG.14A

```
  CATACCCTTTTTGGAGACAAATTATGCACAGTTGCAACTCTTCGTGAAACCTATGGTGAA
H T L F G D K L C T V A T L R E T Y G E
  ATGGCTGACTGCTGTGCAAAACAAGAACCTGAGAGAAATGAATGCTTCTTGCAACACAAA
M A D C C A K Q E P E R N E C F L Q H K
  GATGACAACCCAAACCTCCCCCGATTGGTGAGACCAGAGGTTGATGTGATGTGCACTGCT
D D N P N L P R L V R P E V D V M C T A
  TTTCATGACAATGAAGAGACATTTTTGAAAAAATACTTATATGAAATTGCCAGAAGACAT
F H D N E E T F L K K Y L Y E I A R R H
  CCTTACTTTTATGCCCCGGAACTCCTTTTCTTTGCTAAAAGGTATAAAGCTGCTTTTACA
P Y F Y A P E L L F F A K R Y K A A F T
  GAATGTTGCCAAGCTGCTGATAAAGCTGCCTGCCTGTTGCCAAAGCTCGATGAACTTCGG
E C C Q A A D K A A C L L P K L D E L R
  GATGAAGGGAAGGCTTCGTCTGCCAAACAGAGACTCAAgTGTGCCAGTCTCCAAAAATTT
D E G K A S S A K Q R L K C A S L Q K F
  GGAGAAAGAGCTTTCAAAGCATGGGCAGtGCTCGCCTGAGCCAGAGATTTCCCAAAGCT
G E R A F K A W A V A R L S Q R F P K A
  GAGTTTGCAGAAGTTTCCAAGTTAGTGACAGATCTTACCAAAGTCCACACGGAATGCTGC
E F A E V S K L V T D I T K V H T E C C
  CATGGAGATCTGCTTGAATGTGCTGATGACAGGGCGGACCTTGCCAAGTATATCTGTGAA
H G D L L E C A D D E A D L A K Y I C E
  AATCAaGATTCGATCTCCAGTAAACTGAAGGAATGCTGTGAAAAACCTCTGTTGGAAAAA
N Q D S I S S K L K E C C E K P L L E K
  TCCCACTGCATTGCCGAAGTGGAAAATGATGAGATGCCTGCTGACTTGCCTTCATTAGCT
S H C I A E V E N D E M P A D L P S L A
  GCTGATTTTGTTGAAAGTAAGGATGTTTGCAAAAACTATGCTGAGGCAAAGGATGTCTTC
A D F V E S K D V C K N Y A E A K D V F
  CTGGGCATGTTTTTGTATGAATATGCAAGAAGGCATCCTGATTACTCTGTCGTGCTGCTG
L G M F L Y E Y A R R H P D Y S V V L L
  CTGAGACTTGCCAAGACATATGAAACCACTCTAGAGAAGTGCTGTGCCGCTGCAGATCCT
L R L A K T Y E T T L E K C C A A A D P
  CATGAATGCTATGCCAAAGTGTTCGATGAATTTAAACCTCTTGTGGAAGAGCCTCAGAAT
H E C Y A K V F D E F K P L V E E P Q N
  TTAATCAAACAAAAtTGTGAGCTTTTTAAGCAGCTTGGAGAGTACAAATTCCAGAATGCG
L I K Q N C E L F K Q L G E Y K F Q N A
  CTATTAGTTCGTTACACCAAGAAAGTACCCCAAGTGTCAACTCCAACTCTTGTAGAGGTC
L L V R Y T K K V P Q V S T P T L V E V
  TCAAGAAACCTAGGAAAAGTGGGCAGCAAATGTTGTAAACATCCTGAAGCAAAAAGAATG
S R N L G K V G S K C C K H P E A K R M
  CCCTGTGCAGAAGACTATCTATCCGTGGTCCTGAACCAGTTATGTGTGTTGCATGAGAAA
P C A E D Y L S V V L N Q L C V L H E K
```

FIG. 14B

```
ACGCCAGTAAGTGACAGAGTCACcAAATGCTGCACAGAaTCCTTGGTGAACAGGCGACCA
T P V S D R V T K C C T E S L V N R R P
       TGCTTTTCAGCTCTGGAAGTCGATGAAACATACGTTCCCAAAGAGTTTAATGCTGAAACA
C F S A L E V D E T Y V P K E F N A F T
       TTCACCTTCCATGCAGATATATGCACACTTTCTGAGAAGGAGAGACAAATCAAGAAACAA
F T F H A D I C T L S E K E R Q I K K Q
       ACTGCACTTGTTGAGCTTGTGAAACACAAGCCCAAGGCAACAAAAGAGCAACTGAAAGCT
T A L V E L V K H K P K A T K E Q L K A
       GTTATGGATGATTTCGCAGCTTTTGTAGAGAAGTGCTGCAAGGCTGACGATAAGGAGACC
V M D D F A A F V E K C C K A D D K E T
       TGCTTTGCCGAGGAGGGTAAAAAACTTGTTGCTGCAAGTCAAGCTGCCTTAGGtggaggt C F A E E G K K L V A A S Q A A L G G G
       ggatccGTCCCTCAGAAACCTAAGGTCTCCTTGAACCCTCCATGGAATAGAATATTTAAA
G S V P Q K P K V S L N P P W N R I F K
       GGAGAGAATGTGACTCTTACATGTAATGGGAACAATTTCTTTGAAGTCAGTTCCACCAAA
G E N V T L T C N G N N F F E V S S T K
       TGGTTCCACAATGGCAGCCTTTCAGAAGAGACAAATTCAAGTTTGAATATTGTGAATGCC
W F H N G S L S E E T N S S L N I V N A
       AAATTTGAAGACAGTGGAGAATACAAATGTCAGCACCAACAAGTTAATGAGAGTGAACCT
K F E D S G E Y K C Q H Q Q V N E S E P
       GTGTACCTGGAAGTCTTCAGTGACTGGCTGCTCCTTCAGGCCTCTGCTGAGGTGGTGATG
V Y L E V F S D W L L L Q A S A E V V M GAGGGCCAGCCCCTCTTCCTCAGGTGCCATGGTTGGAGGAACTGGGATGTGTACAAGGTG
E G Q P L F L R C H G W R N W D V Y K V
       ATCTATTATAAGGATGGTGAAGCTCTCAAGTACTGGTATGAGAACCACAACATCTCCATT
I Y Y K D G E A L K Y W Y E N H N I S I
       ACAAATGCCACAGTTGAAGACAGTGGAACCTACTACTGTACGGGCAAAGTGTGGCAGCTG
T N A T V E D S G T Y Y C T G K V W Q L
       GACTATGAGTCTGAGCCCCTCAACATTACTGTAATAAAAGCTCCGCGTGAGAAGTACTGG
D Y E S E P L N I T V I K A P R E K Y W

CTATAGTAAGAATTC
L * *
```

FIG.14C

FUSION POLYPEPTIDES

This application claims the benefit of U.S. Provisional Application No. 60/022,689, filed Jul. 26, 1996.

FIELD

The invention relates to fusion polypeptides. It concerns fusion polypeptides comprising an IgE-binding domain and a human serum albumin (HSA) component and salts thereof. It also concerns polynucleotides and physiologically functional equivalent polypeptides which are intermediates in the preparation of such fusion polypeptides; appropriate recombinant expression vectors therefor, corresponding procaryotic and eucaryotic expression systems, and processes for synthesizing the fusion polypeptides.

BACKGROUND

The interaction between immunoglobulin E (IgE) and its receptors has an established role in the defense against parasitic infections in humans (M. Capron and A. Capron. *Science* 264 [1994] 1876–1877). In industrialized countries, however, with improved hygienic conditions, the encounter with parasites is less frequent than the disturbance of the IgE network by over-production of IgE in response to environmental allergens. resulting in allergies and other IgE- or IgE-receptor- mediated disease states.

IgE is the primary antibody involved in initiation of an immediate allergic response and is a major participant in the maintenance of the late phase response. IgE is synthesized in B lymphocytes and exerts its effects after binding to the high affinity receptor for IgE, i.e. FcϵRI, which is found on the surface of allergy effector cells such as mast cells, basophils and eosinophils. IgE also exerts inducer functions through binding to its receptor on antigen presenting cells such as Langerhans cells, B cells and monocytes (G. C. Mudde et al., *Allergy* 50 [1995] 193–199).

An allergic response or condition is manifested when IgE molecules bind to the surface of allergy effector cells via the IgE receptor, FcϵRI, and become cross-linked by allergen, thereby effecting signalling to initiate degranulation of cytoplasmic granules in the cells, with accompanying release of mediators of allergy such as histamine, serotonin, prostaglandins and cytokines, and consequent local tissue edema and influx of inflammatory cells. An alternate means of stimulating allergy and associated conditions is the interaction of the IgE receptor, FcϵRI, with circulating autoantibodies against FcϵRI.

FcϵRI typically exists as a tetramer comprising an α-, a β- and two γ-chains (i.e. "subunits"), although on monocytes and Langerhans cells, the β-subunit is absent.

The IgE binding site of FcϵRI has been shown to be contained entirely within its α-subunit (referred to as FcϵRIα) (J. Hakimi et al., *J. Biol. Chem.* 265 [1990] 22079–22081; U. Blank et al., *J. Biol Chem.* 266 [1991] 2639–2646). Recombinant "knockout" mice genetically deleted for the entire α-subunit have been found to be unable to mount an allergic response to allergen challenge (D. Dombrowicz et al., *Cell* 75 [1993] 969–976).

FcϵRIα is a heavily glycosylated polypeptide of molecular weight about 60 kD, comprising a hydrophobic transmembrane domain as well as hydrophilic extracellular ("ecto-") and cytoplasmic domains which are exposed to the outer surface of the cell. The IgE binding capability of FcϵRIα has been been further localized to its extracellular portion (J. Hakimi et al. [11990], supra; Leder et al., U.S. Pat. No. 4,962,035). It is possible to produce a soluble, secretable molecule by excising the transmembrane portion and sequences downstream therefrom (C. Ra et al., *Int. Immunol.* 5 [1993] 47–54); and the resulting truncation, consisting essentially of the human FcϵRIα extracellular domain, has IgE-binding activity in vitro and in vivo (M. Haak-Frendscho et al., *Immunol.* 151 [1993] 351–358: amino acid residues 1–204 of FcϵRIα fused to a truncated IgGl H chain C region; C. Ra. et al. [1993] supra: residues 1–172 of FcϵRIα therein, corresponding to residues 26–197 of SEQ. ID. NO. 1 hereof). Structural features of this fragment include two potential disulfide bridges and seven potential glycosylation sites (M. Haak-Frendscho et al. [1993], supra).

Therefore, truncations of FcϵRIα consisting essentially of the extracellular domain can potentially be administered therapeutically to a mammal to bind serum IgE in order to prevent its binding to its high affinity receptor on allergy effector cells, and also for suppressing de novo IgE biosynthesis in human lymphocytes (Y. Yanagihara et al., *J. Clin. Invest.* 94 [1994] 2162–2165).

However, effective use of an IgE-binding polypeptide such as the extracellular domain of FcϵcRIα for systemic treatment of IgE- or IgE receptor- mediated allergic disorders in mammals has been hindered by its extreme transience in vivo due to rapid clearance from circulating plasma. Considering that IgE- or IgE receptor- mediated diseases account for 10–20% of physician-patient contact, an effective treatment would constitute a significant benefit to patients suffering from such conditions and an important advance in the clinical treatment of IgE- and IgE receptor-mediated disorders such as allergy and allergy-related conditions.

It would therefore be beneficial to obtain an IgE-binding polypeptide having prolonged effective serum life and thus improved clinical utility in the treatment of allergy, and in particular the systemic treatment of atopic dermatitis, atopic asthma and chronic urticaria, as well as improved activity in an efficient, cost-effective manner.

SUMMARY

It has now been found that by fusing an IgE-binding domain to a human serum albumin (HSA) component, fusion polypeptides can be obtained having extended serum half-life relative to the IgE-binding domain alone, without loss of IgE-binding activity, resulting in IgE-binding polypeptides indicated for use in the systemic treatment of allergy and other IgE-mediated disorders. Systemically administered IgE-binding polypeptide will bind to serum IgE as well as to circulating auto-antibodies against the IgE receptor, FcϵRIα, preventing them from binding to cell-bound FcϵRIα, and thus preventing and/or inhibiting an allergic reaction and its associated manifestations.

It has further been found that significant improvements in IgE-binding activity can be obtained by using fusion polypeptides of the invention comprising more than one IgE-binding domain per molecule. For example, a "dimer" molecule of the invention has been found to have significantly increased IgE-binding activity relative to a "monomer" of the invention.

The term "dimer" herein refers to a fusion polypeptide of the invention possessing two IgE-binding domains. The term "monomer" refers to a fusion polypeptide of the invention possessing one IgE binding domain. The monomer or dimer may be constructed of a single or multiple HSA components. For example, a monomeric fusion polypeptide of the invention may comprise an IgE-binding domain fused at either its amino or carboxy terminus to an HSA component. Alternatively, the monomer may comprise an IgE-binding domain fused at both of its termini to HSA components. A dimeric fusion polypeptide according to the invention may comprise, for example, two IgE-binding domains fused via the carboxy terminus of one and the amino terminus of the other to an intervening HSA component. Alternatively, the dimer may comprise, in addition to its two IgE-binding domains, multiple HSA components.

It has further been found that a dimer molecule of the invention possesses unexpectedly favorable activity.

The invention therefore is directed to fusion polypeptides and salts thereof comprising at least one IgE-binding domain fused to at least one HSA component; preferably. to monomeric fusion polypeptides, wherein a single IgE-binding domain is fused to one or more HSA components, or to multimeric fusion polypeptides, wherein two or more IE-binding domains are fused to at least one HSA component; more preferably, dimers possessing two IgE-binding domains and at least one HSA component.

The invention is further directed to polynucleotide intermediates therefor.

The term "fused" or "fusion" herein refers to polypeptides in which:

(i) a given functional domain (i.e. an IgE-binding domain) is bound at its carboxy terminus by a covalent (preferably, peptide, i.e. amide) bond either to the amino terminus of another functional domain (i.e. an HSA component) or to a linker peptide which itself is bound by a covalent (preferably, peptide) bond to the amino terminus of the other functional domain; and/or, (ii) a given functional domain (i.e. an IgE-binding domain) is bound at its amino terminus by a covalent (preferably, peptide, i.e. amide) bond either to the carboxy terminus of another functional domain (i.e. an HSA component) or to a linker peptide which itself is bound by a covalent (preferably, peptide) bond to the carboxy terminus of the other functional domain.

Similarly, "fused" when used in connection with the polynucleotide intermediates of the invention means that the 3'-[or 5'-] terminus of a nucleotide sequence encoding a first functional domain is bound to the respective 5'-[or 3'-] terminus of a nucleotide sequence encoding a second functional domain, either by a covalent bond or indirectly via a nucleotide linker which itself is covalently bound preferably at its termini to the first functional domain-encoding polynucleotide and the second functional domain-encoding polynucleotide.

Preferably, the fusion polypeptide or its salt is a monomer or a dimer; when it is a dimer it comprises two IgE-binding domains fused to an HSA component, such as a first IgE-binding domain fused at its carboxy terminus to the amino terminus of an HSA component, and a second IgE-binding domain fused at its amino terminus to the carboxy terminus of that HSA component.

The fusion polypeptides of the invention may also comprise further functional domains in addition to IgE-binding domains and HSA components, e.g. full length or truncated (e.g. soluble, extracellular fragments of) human proteins, such as cytokines or the amino-terminal fragment of urokinase. These additional functional domains may themselves serve as linker peptides, for example, for joining an IgE-binding domain to another IgE-binding domain or to an HSA component; alternatively, they may be located elsewhere in the fusion molecule, e.g. at the amino or carboxy terminus thereof.

Examples of fusion polypeptides of the invention may be represented by the following formulas:

$R_1$-L-$R_2$ I.

$R_2$-L-$R_1$ II.

$R_1$-L-$R_2$-L-$R_1$ III.

$R_{1\text{-}L\text{-}R1}$-L-$R_2$ IV.

$R_2$-L-$R_1$-L-$R_1$ V.

wherein $R_1$ is the amino acid sequence of an IgE-binding domain, $R_2$ is the amino acid sequence of an HSA component, each L is independently a covalent (preferably, peptide) bond, or is a peptide linker which is bound by a covalent (preferably, peptide) bond to a terminus of $R_1$ and/or $R_2$, whereby the above molecule fragments are read directionally, i.e. with the left side corresponding to the amino terminus and the right side to the carboxy terminus of the molecule.

It has been found that IgE binding is at high levels when the fusion polypeptide is led by an IgE-binding domain; that is, when the IgE binding domain constitutes the N-terminal portion of the mature fusion protein (such as in compounds of formulae I, III and IV, above). A particularly preferred embodiment of the invention comprises a dimer of formula III above, i.e. wherein the protein region which leads expression is an IgE-binding domain, fused at its carboxy terminus to the amino terminus of an HSA component, which in turn is itself fused at its carboxy terminus to the amino terminus of a second IgE-binding domain. When there is more than one $R_1$ moiety, or more than one $R_2$ moiety, or more than one L moiety, these moieties can be, but are not necessarily, identical.

Preferably the fusion polypeptides of the invention comprise at least one soluble, secretable mammalian IgE-binding domain fused to at least one HSA component, and pharmaceutically acceptable salts thereof.

The invention is further directed to a method for the prevention and/or treatment of IgE- or IgE-receptor- mediated disorders, and in particular, allergic reactions such as atopic dermatitis, atopic asthma and chronic urticaria, comprising the administration of the fusion polypeptides of the invention or pharmaceutically acceptable salts thereof to a subject in need of such treatment; and to pharmaceutical compositions comprising the fusion polypeptides of the invention or pharmaceutically acceptable salts thereof, together with at least one pharmaceutically acceptable carrier or diluent.

The invention is further directed to physiologically functional equivalents of the fusion polypeptides of the invention which are intermediates in the synthesis of the polypeptides; to polynucleotides which are intermediates in the preparation of the fusion polypeptides or physiologically functional equivalents thereof as defined above; to oligonucleotide intermediates to be used to construct them; to the peptides encoded by such oligonucleotides; to recombinant vectors for expressing the fusion molecules; to procaryotic or eucaryotic (especially, mammalian) expression systems; and to processes for preparing the fusion polypeptides or physiologically functional equivalents thereof using such expression systems.

Description of SEO. ID. NOs. and Related Definitions

SEQ. ID. NO. 1: Amino acid sequence of dominant form of full length native human FcεRIα, including signal sequence.

The term "pre-IgE$^R$" refers to residues Met$_1$-Leu$_{204}$ of SEQ. ID. NO. 1. The term "IgE$^R$" refers to the mature form of pre-IgE$^R$ and constitutes residues Val$_{26}$-Leu$_{204}$ of SEQ. ID. NO. 1 (i.e. the extracellular domain of FcεRIα).

SEQ. ID. NO. 2: Amino acid sequence of dominant form of native prepro-HSA (referred to herein as "prepro HSA I"), comprising residues Met$_1$-Leu$_{609}$.

The dominant form of the mature native protein (referred to herein as "HSA I") is represented by residues Asp$_{25}$-Leu$_{609}$ of SEQ. ID. NO. 2.

The term "prepro-HSA II" represents a truncation of the native sequence by one amino acid (Leu$_{609}$) at the carboxy terminus, and therefore refers to residues Met$_1$-Gly$_{608}$ of SEQ. ID. NO. 2.

The mature form of prepro-HSA II, referred to herein as "HSA II", is represented by residues Asp$_{25}$-Gly$_{608}$ of SEQ. ID. NO. 2.

SEQ. ID. NO. 3: Amino acid sequence encoded by the EcoRI fragment of plasmid R-H-R/SK#50 prepared in Example 5, comprising: "pre-IgE$^R$" sequence at residues 1–204; linker AlaSer(Gly)$_4$Ser (referred to hereinafter as "L$_1$") at residues 205–211; HSA II sequence at residues 212–795; linker (Gly)$_3$Ser (referred to hereinafter as "L$_2$") at residues 796–799; and the "IgE$^R$" sequence at residues 800–978.

A mature dimeric fusion polypeptide of the invention, referred to herein as "IgE$^R$-L$_1$-HSA II-L$_2$-IgE$^R$" or, alternatively, as "IgE$^R$-HSA-IgE$^R$ Dimer", expressed from CHO cells in the manner described in Example 7, has the amino acid sequence Val$_{26}$-Leu$_{978}$ of SEQ. ID. NO. 3.

SEQ. ID. NO. 4: Nucleotide sequence of the EcoRI fragment of plasmid R-H-RISK #50 of Example 5, comprising: a polynucleotide sequence encoding "pre-IgE$^R$" at positions 10–621; an oligonucleotide encoding L$_1$ at positions 622–642; a polynucleotide encoding HSA II at positions 643–2394; an oligonucleotide encoding L$_2$ at positions 2395–2406; and a polynucleotide encoding "IgE$^R$" at positions 2407–2943; with 2 stop codons at positions 2944–2949.

Restriction sites at the ends of the coding fragments and in the linker regions are at positions 1–6; 622–627; 637–642; 2387–2393; 2401–2406; and 2950–2955. A Kozak sequence is at nucleotide positions 7–9.

Point mutations differing from the consensus HSA nucleotide sequence are at positions 804, 1239; 1290; 1446, 1815, 2064 and 2079. Because the point mutations are in the wobble position, they do not affect the amino acid sequence.

Seq. ID. NO. 5: Nucleotide sequence of the dominant form of native prepro-HSA corresponding to FIG. 12 and to the amino acid sequence of SEQ. ID. NO. 2.

SEQ. ID. NO. 6: Nucleotide sequence of the dominant form of full length native human FcεRIα including signal sequence, corresponding to FIG. 13 and to the amino acid sequence of SEQ. ID. NO. 1.

SEQ. ID. NO. 7: HSA, IgE$^R$ and mutagenic sequencing oligonucleotides

DESCRIPTION OF THE FIGURES

In the following Figures, the indicated molecules are read directionally, i.e. the left side corresponding to the amino (or 5'-) terminus and the right side corresponding to the carboxy (or 3'-) terminus.

(C) Serum half life of free HSA I from (A) compared with that of dimeric fusion polypeptide ("IgE$^R$-HSA-IgE$^R$") from (B) by normalizing to 1 with respect to serum concentrations at 10 minutes after injection.

Figure 2:
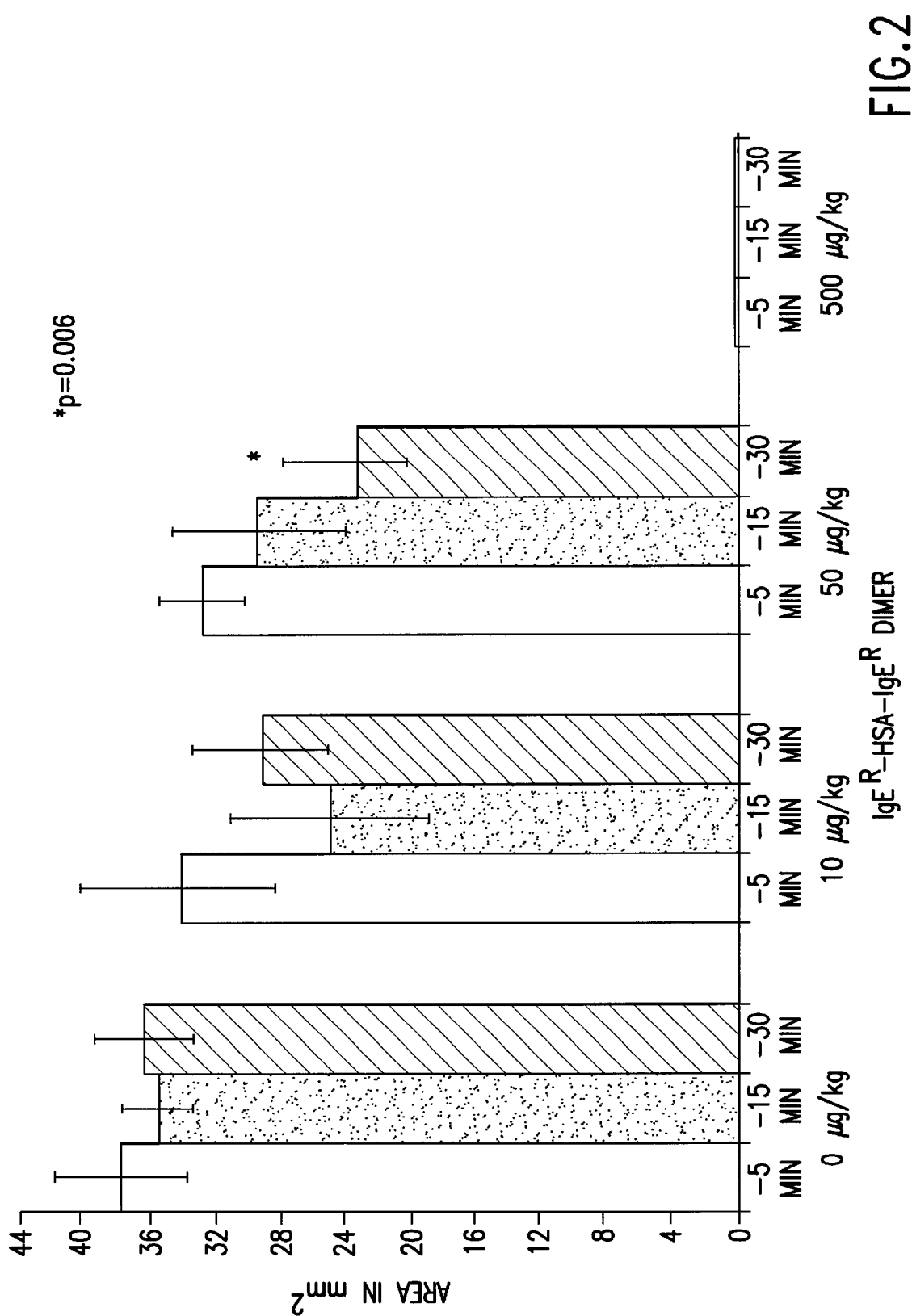

FIG. 2: Extravasation resulting from passive cutaneous anaphylaxis reaction in mice administered intravenous serial dilutions (10 μg/kg, 50 μg/kg or 500 μg/kg) of IgE$^R$-L$_1$-HSA II-L$_2$-IgE$^R$ polypeptide ("IgE$^R$-HSA-IgE$^R$ Dimer") prepared as described in Example 7 (the control group receiving 0 μg/kg); area in mm$^2$; at intervals of 5, 15 or 30 minutes prior to sensitization by intradermal injection of monoclonal mouse IgE anti-dinitrophenyl (DNP) antibody and subsequent challenge with DNP-bovine serum albumin solution containing 1% Evans blue.

FIG. 3: Schematic representation of three fusion polypeptides of the invention (two monomers and one dimer), with the polypeptide linkers also shown:

I. Monomers:
(1.) HSA-leading monomer comprising HSA II (referred to in the Figure as "HSA") fused via L$_2$ ("GGGS") (SEQ. ID. NO. 37) to IgE$^R$. The nucleotides encoding positions Leu$_{607}$Gly$_{608}$ of HSA II contain a unique MstII site as indicated, and the nucleotides encoding GlySer of L$_2$ contain a BamHI site (encoded amino acids underlined);

(2.) IgE-binding domain-leading monomer comprising IgE$^R$ fused at its carboxy terminus via L$_1$ (i.e. "ASGGGGS") (SEQ. ID. NO. 38) to HSA II (referred to in the Figure as "HSA"). The oligonucleotide encoding L$_1$ contains a NheI site and a BamHI site respectively (encoded amino acids AlaSer and GlySer of L$_1$ are underlined).

II. Dimer: IgE-binding domain-leading dimer comprising a first IgE$^R$ fused at its carboxy terminus via L$_1$ to the amino terminus of HSA II (referred to in the Figure as "HSA"), the carboxy terminus of which is fused to a second IgE$^R$ via L$_2$ with restriction sites in the encoding polynucleotide as described above for the monomer.

FIG. 4: PCR primers to truncate full length human FcεRIα cDNA (referred to as "IgE Receptor cDNA") to obtain DNA encoding:

(i) IgE$^R$[BamHI site added to 5' end of coding strand for FcεRIo by oligonucleotide #18; and stop codon and EcoRI and SalI sites added to 3' end of non-coding strand by oligonucleotide #19];

(ii) pre-IgE$^R$[oligonucleotide #20 adding SstI, EcoRI, and Kozak sites to 5' end of coding strand for FcεRIα; oligonucleotide ™31 adding NotI and NheI (and deleting a second NheI site) in non-coding strand for FcεRIα];

(iii) pre-IgE$^R$[oligonucleotides #20 and #19 used as described above]:

(A.) "HSA-leading": subcloning of (i) above into SK vector, providing cloning vector TA clone pEK1 used in construction of HSA II-leading monomer;

(B.) "IgE$^R$-leading": subcloning of (ii) into SK vector, providing construct IgER/TA#1 used to prepare IgE$^R$-leading monomer;

(C.) "IgE$^R$ alone": subcloning of (iii) into SK vector, providing construct IgE$^R$ FL/TA#34 used in expression of mature IgE$^R$ for use as a standard.

Double asterisks represent two stop codons.

Figure 5:
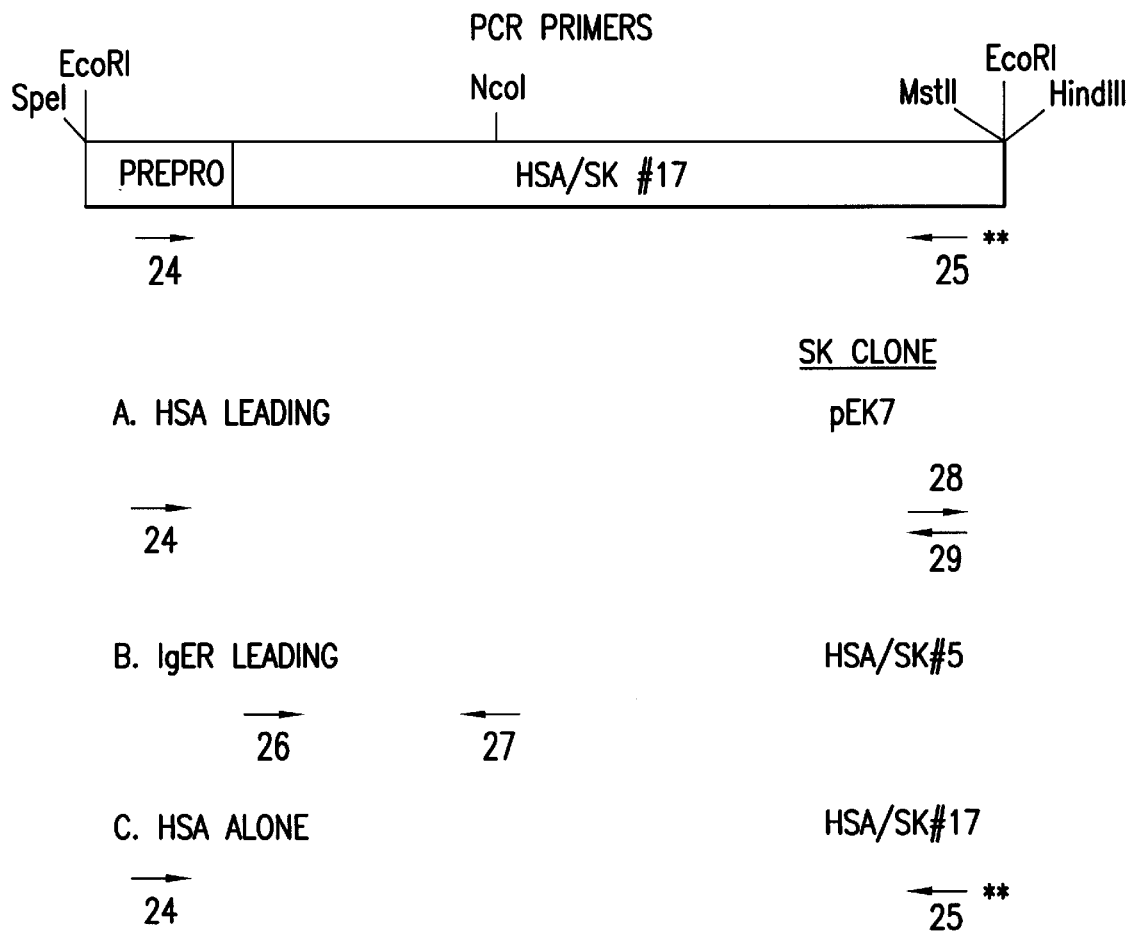

FIG. 5: PCR primer pairs to truncate full length human prepro-HSA I cDNA to yield cDNA encoding:

(i) prepro-HSA II fused at carboxy terminus to $L_2$[oligonucleotide #24 adding SpeI, EcoRI and Kozak sequence to 5'-end of coding strand; oligonucleotides #28 and #29 adding a linker encoding MstII and HindIII sites at the 3' terminus of HSA II);

(ii) $L_1$ fused to 5' terminus of HSA II [oligonucleotide #27 containing NcoI site in non-coding strand];

(iii) Prepro-HSA I [oligonucleotide #24 used as above; and oligonucleotide #25 adding stop, EcoRI and HindIII sites to 3' end of non-coding strand]:

(A.) "HSA leading": subcloning of (i) into SK vector, providing pEK7 used to construct HSA II- leading monomer;

(B.) "IgER leading": subcloning of (ii) into SK vector, providing HSA/SK#5 used to construct $IgE^R$ leading monomer;

(C.) "HSA alone": subcloning of (iii) into SK vector, providing HSA/SK#17 encoding mature native human serum albumin protein (i.e. HSA I) for use as a standard.

FIG. 6: Human serum albumin (HSA) sequencing oligonucleotides #1–10, 12, 16, 17, 22 and 30 (SEQ. ID. NOS. 7–21), used to sequence materials cloned in TA and after linkage to IgE-binding fragments.

FIG. 7: IgE receptor sequencing oligonucleotides #11, 13 and 23 (SEQ. ID. NOS. 22–24), used to sequence fragments cloned in TA and after linkage to HSA component.

FIGS. 8A–8C:
(A) Mutagenic oligonucleotides #14 and #15 (SEQ. ID. NOS. 25–26), for human serum albumin;
(B) and (C) PCR and linker oligonucleotides #18–20, 24–29 and 31 (SEQ. ID. NOS. 27–36), for constructing fusion polypeptides.

Figure 9:
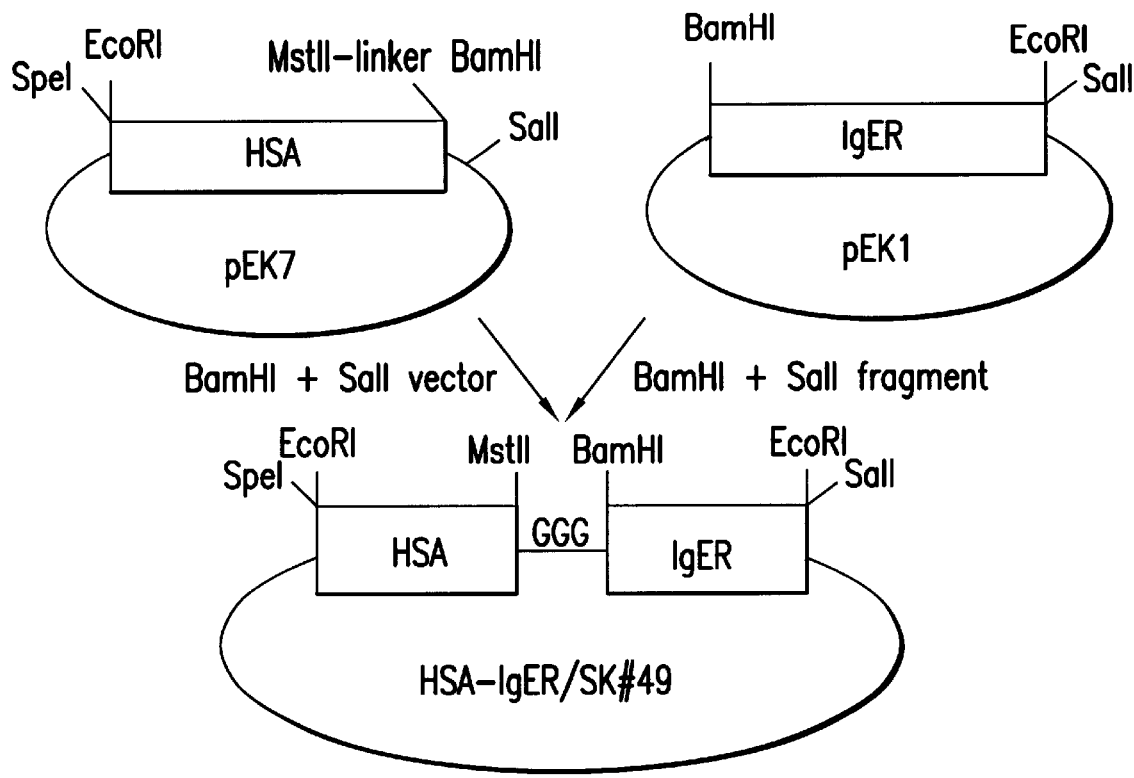

FIG. 9: Construction of vector HSA-$IgE^R$/SK#49, comprising a polynucleotide encoding prepro-HSA II (referred to in the Figure as "HSA") fused at 3'-termninus via oligonucleotide encoding linker $L_2$ (represented in FIG. 9 by "GGG") to 5'-terminus of polynucleotide encoding $IgE^R$ (referred to in the Figure as "IgER"), by ligating the BamHI, SalI fragment of pEK1 into BamHI, SalI-cut pEK7.

FIG. 10: Construction of vector $IgE^R$-HSA/SK#1, comprising a polynucleotide encoding pre-$IgE^R$ (referred to in the Figure as "IgER") fused at 3'-terminus via oligonucleotide for linker $L_1$ (represented by "GGG") to 5'-terminus of polynucleotide encoding HSA II ("HSA"), by ligating the SstI, NheI fragment of IgER/TA#1 into SstI,NheI - cut HSA/SK#5.

FIG. 11: Construction of vector HSA-IgER Pst Sal/SK#37, comprising a polynucleotide encoding HSA II (indicated by "HSA3") which is fused at the 3' terminus via oligonucleotide for $L_2$ (not depicted) to 5'-terminus of polynucleotide encoding $IgE^R$ (indicated as "IgER"), by ligating the PstI, SalI fragment of HSA-IgER/SK#49 into SK vector. Also shown is construction of a vector R-H-R/SK#50 comprising a polynucleotide encoding pre-$IgE^R$ (referred to as "IgER") fused at its 3' terminus via oligo for $L_1$ (not depicted) to 5'-terminus of polynucleotide encoding HSA II ("HSA"), which in turn is fused via oligonucleotide for $L_2$ (not depicted) to a polynucleotide encoding $IgE^R$ ("IgER"). The vector is prepared by ligating the PstI,KpnI fragment of HSA-IgER Pst Sal/SK#37 into PstI,KpnI-cut IgER-HSA/SK#1.

FIGS. 12A–12B: Nucleotide sequence of human serum albumin and amino acid sequence corresponding to SEQ. ID. NO. 2 and SEQ. ID. NO. 5.

FIG. 13: Nucleotide sequence of $IgE^R$ and amino acid sequence corresponding to SEQ. NO. 1 and SEQ. ID. NO. 6.

FIGS. 14A–14C: Nucleotide and amino acid sequences of the EcoRI fragment of R-H-R/SK#50 corresponding to SEQ. ID. NO. 3 and SEQ. ID. NO. 4, encoding the R1-HSA-R1 dimeric fusion protein. The HSA sequence is shown in italics. Linker sequences are shown in lower case. Point mutations differing from the consensus HSA nucleic acid sequence are shown in bold lower case. Because the point mutations are in the wobble position, they do not affect the amino acids sequence. Restriction sites at the ends of the fragments and in the linker region are underlined.

FIG. 15: SDS-PAGE of purified mature fusion polypeptide of Example 7:

Total amounts applied to gel: 8 μg (lane 1), 6 μg (lane 2), 4 μg (lane 3) and 2 μg (lane 4); molecular weight standards: 97.4, 66.2, 45, 31, 21.5 and 14.4 kDa (lane 5).

DETAILED DESCRIPTION

The invention concerns fusion polypeptides and salts thereof, comprising at least one IgE-binding domain fused to at least one HSA component.

The term "IgE-binding domain" refers to an amino acid sequence capable of binding or otherwise associating with mammalian, e.g. human IgE in a manner preventing the binding of IgE to its receptor, FcεRI.

F The cDNA and deduced amino acid sequence of human FcεRIα are known (J.Kochan et al., Nucleic Acids Research 16 [1988] 3584; and Leder et al., U.S. Pat. No. 4,962,035). Human FcεRIα encodes an $NH_2$-terminal signal peptide [amino acid residues (including the first Met) $Met_1$-$Ala_{25}$], two immunoglobulin-like extracellular domains (residues $Val_{26}$-$Leu_{204}$), a hydrophobic transmembrane region ($Gln_{205}$-$Ile_{224}$), and a hydrophilic cytoplasmic tail (residues $Ser_{225}$-$Asn_{257}$) (with reference to SEQ. ID. NO. 1). The signal peptide is cleaved during intracellular processing. The full length amino acid sequence of the dominant form of native human FcεRIα is included herein as SEQ. ID. NO. 1.

"$IgE^R$" herein refers to amino acid sequence $Val_{26}$-$Leu_{204}$ of SEQ. ID. NO. 1 (encoding the extracellular domain); and the term "pre-$IgE^R$" refers to residues $Met_1$-$Leu_{204}$ of SEQ. ID. NO. 1 (encoding the signal sequence upstream of the extracellular domain).

The IgE-binding domain is e.g. an amino acid sequence having at least 80%, more preferably at least 85%, more preferably at least 95%, or most preferably at least 99%, homology with $IgE^R$ as defined above (homology is calculated as the % identity between the native sequence and the altered sequence, as a function of total sequence length of the native molecule, after aligning the sequences and introducing gaps, if necessary, to achieve the maximum percent sequence identity).

In a subgroup of fusion polypeptides of the invention the IgE-binding domain component is (Xa)

wherein (Xa) is:

(a) $IgE^R$; or (b) a naturally occurring allele of $IgE^R$, or (c) a truncation of (a) or (b) at the carboxy terminus by 1–12 (e.g. 1–10, 1–7 or 1–4) amino acids; or p (d) a variant of (a), (b) or (c).

By "variant" is meant:

the sequence of (a), (b) or (c) as modified by one or more deletions (which are other than truncations at the carboxy terminus) of up to 10 (e.g. 1–7 or 1–5 amino acids;

insertions of a total of up to 10 (e.g. 1–5) amino acids internally within the amino acid insertions of a total of up to 10 (e.g. 1–5) amino acids internally within the amino acid sequence, or of up to a total of 100 amino acids at either terminus; or conservative substitutions of a total of up to 15 (e.g.1–5) amino acids.

The IgE-binding domain is more preferably (Xb)

wherein (Xb) is:
(a) IgE$^R$;
(b) a truncation of IgE$^R$ at the carboxy terminus by 1–7 amino acids; or
(c) a variant of (a) or (b).

The IgE-binding domain is even more preferably (Xc)

wherein (Xc) is:
(a) IgE$^R$; or
(b) a truncation of IgE$^R$ at the carboxy terminus by 1–7 amino acids (e.g. the sequence Val$_{26}$-Ala$_{197}$ with reference to SEQ. ID. NO. 1).

The IgE-binding domain is most preferably IgE$^R$.

Preferably, any homolog, truncation or variant is prepared recombinantly as a "secretable" polypeptide, namely the mature peptide sequence encoding the IgE-binding domain can be secreted from the host cell in which it (or a precursor form such as a pre-form) is synthesized from a polynucleotide.

The other major constituent of the recombinant fusions of the invention, human serum albumin (HSA), constitutes the most abundant plasma protein, contributing 60% on a per weight basis of the total protein content of plasma. A molecule of human serum albumin consists of a single non-glycosylated polypeptide chain of 585 amino acids of molecular weight 66.5 kDa. A feature specific to albumin is its complex disulfide bond pattern (F. F. Clerc et al., *J. Chromatogr*. 662 [1994] 245–259). Human serum albumin is widely distributed throughout the body, in particular in the intestinal and blood compartments where it is mainly involved, as the most abundant protein of the serum, in the maintenance of osmolarity and plasma volume. Furthermore, it is slowly cleared by the liver and displays an in vivo half-life of 14–20 days in humans (T. A. Waldmann, "*Albumin Structure, Function and Uses*", Pergamon Press [1977] 255–275). Human serum albumin is devoid of enzymatic or immunological function. It is a natural carrier involved in the endogenous transport and delivery of various natural as well as therapeutic molecules (H. Lu et al., FEBS Lett. 356 [1994] 56–59; WO 93/15199; EP 648499; P. Yeh et al., *PNAS USA* 89 [1992] 1904–1908; EP 413622).

Human cells synthesize serum albumin initially in the form of a prepro- polypeptide. A signal sequence of 18 amino acids (including the first Met) is removed when the protein passes through the lumen of the endoplasmic reticulum, leaving still 6 amino acids at the N-terminus (in the predominant form: Arg-Gly-Val-Phe-Arg-Arg) which are then subject to proteolytic excision during or immediately following transport through the secretory apparatus.

Human serum albumin is well-known to be polymorphic (D. C. Carter and J. X. Ho, *Adv. Prot. Chem.* 45 [1994] 153–203). For example, albumin Naskapi has $Lys_{372}$ in place of $Glu_{372}$, and proalbumin Christchurch has an altered pro- sequence, i.e. $Glu_{24}$ instead of $Arg_{24}$ (Latta et al., U.S. Pat. No. 5,100,784, incorporated by reference herein).

The complete amino acid sequence of the dominant form of naturally occurring protein, referred to herein as "prepro-HSA I", is known (A. Dugaiczyk et al., *PNAS USA* 79 [1982] 71–75) (SEQ. ID. NO. 2). The dominant form of the mature protein ("HSA I") is represented by $Asp_{25}$-$Leu_{609}$ of SEQ. ID. NO. 2.

The HSA carrier of the fusion polypeptide of the invention may be an amino acid sequence having at least 80%, more preferably at least 85%, even more preferably at least 95%, or most preferably at least 99%, homology with residues 25–609 of SEQ. ID. NO. 2 (i.e. HSA I) (homology is calculated as the % identity between the native sequence and the altered sequence, as a function of total sequence length of the native molecule, after aligning the sequences and introducing gaps, if necessary, to achieve the maximum percent sequence identity).

In a subgroup of fusion polypeptides of the invention, the HSA component is (Ya)

wherein (Ya) is:

(a) HSA I; or (b) a naturally occurring allele of (a); or (c) a truncation of (a) or (b) at the carboxy terminus thereof by 1–10 (e.g.1–5, or 1 or 2) amino acids; or (d) a truncation of (a) terminating at amino acid residue n, where n is 369 to 419, and especially where n is 373, 387, 388, 389, 390 and 407 ( U.S. Pat. No. 5,380,712, incorporated by reference); or (e) a variant of (a), (b), (c) or (d).

By "variant" is meant:

the sequence of (a), (b), (c) or (d) as modified by one or more deletions (which are other than truncations at the carboxy terminus) of up to 10 (e.g. 1–7, or 1–5) amino acids;

insertions of a total of up to 10 (e.g. 1–5) amino acids internally within the sequence, or of up to a total of 100 amino acids at either terminus; or conservative substitutions of a total of up to 15 (e.g. 1–5) amino acids.

The HSA component is more preferably (Yb)

wherein (Yb) is:

(a) HSA I; or (b) a naturally occurring allele of (a); or (c) a truncation of (a) or (b) at the carboxy terminus thereof by 1–10 (e.g. 1–5, or 1 or 2) amino acids); or (d) a variant of (a), (b) or (c).

The HSA component is even more preferably (Yc)

wherein (Yc) is:

(a) HSA I, or (b) a truncation of HSA I at the carboxy terminus thereof by 1–10 (e.g., 1) amino acids (an example of such a truncation is "HSA II", which is the amino acid sequence represented by $Asp_{25}$-$Gly_{608}$ of SEQ. ID. NO. 2.)

In an even more preferred subgroup, the HSA component is HSA I or HSA II, particularly HSA II.

Especially preferred is the fusion polypeptide of Example 7, especially without leader sequence, i.e. the polypeptide $Val_{26}$-$Leu_{978}$ of SEQ. ID. NO. 3.

Preferably, any homolog, truncation or variant of native HSA which is used to prepare a fusion protein of the invention will be devoid of enzymatic function; and will not prevent or inhibit binding of the IgE-binding domain to serum IgE. It is further preferred that any such homolog or variant will have a serum half-life of at least 14 days.

With respect to either the IgE-binding domain or HSA component, the term "conservative substitutions" refers to the substitution of one or more amino acids by others having similar properties such that one would expect at least the secondary structure, and preferably the tertiary structure of the polypeptide, to be substantially unchanged. For example, typical such substitutions include alanine or valine for glycine, asparagine for (glutamine. serine for threonine and arginine for lysine. All of the amino acids (except for glycine) are preferably naturally-occurring L-amino acids.

Preferably each IgE-binding domain is at least 95% homologous to IgE$^R$, and each HSA component is at least 95% homologous to HSA I.

In other preferred subgroups:
  each IgE-binding domain is preferably (Xa), and each HSA component is (Ya), or more preferably (Yb), or even more preferably (Yc), as defined above;
  each IgE-binding domain is more preferably (Xb), and each HSA component is (Ya), or more preferably (Yb), or even more preferably (Yc), as defined above;
  each IgE-binding domain is even more preferably (Xc), and each HSA component is (Ya) or more preferably (Yb), or even more preferably (Yc).

In a further preference, the IgE-binding domain is IgE$^R$ and the HSA component is (Ya), or more preferably (Yb), or even more preferably (Yc), as defined above, and is most preferably HSA I or HSA II, in particular HSA II.

The preferences expressed above also apply in particular to the polypeptides of each of formulae I, II, III, IV and V herein.

Preferred polypeptides of the invention are those comprising a first molecule of IgE$^R$ which is fused via its carboxy terminus to the amino terminus of a molecule of HSA II, which HSA II is fused at its carboxy terminus to the amino terminus of a second molecule of IgE$^R$ (IgE$^R$ being residues Val$_{26}$-Leu$_{204}$ of SEQ. ID. NO. 1; and HSA II being residues Asp$_{25}$-Gly$_{608}$ of SEQ. ID. NO. 2).

Particularly preferred polypeptides of the invention comprise dimers of formula III hereinabove wherein each R$_1$ is IgE$^R$ and R$_2$ is HSA II. Especially preferred are the dimers of formula III wherein each L is 1–25 amino acids.

Any peptide linker (expressed as "L" in formulae I-V herein) preferably allows independent folding and activity of the IgE-binding domain; is free of a propensity for developing an ordered secondary structure which could interfere with the IgE-binding domain or cause an immunological reaction in the patient, and has minimal hydrophobic or charge characteristics which could interact with the IgE-binding domain.

P The peptide linker is preferably 1–500 amino acids; more preferably 1–250; and even more preferably 1–100 (e.g. 1–25, 1–10, 1–7 or 1–4) amino acids. The linker is preferably linear, i.e. non-branched. In general, peptide linkers comprising Gly, Ala and Ser can be expected to satisfy the criteria for a linker. For example, linkers of the present invention include: GlyGlyGlySer ("$L_1$" herein) and AlaSerGlyGlyGlyGlySer ("$L_2$" herein). Linkers of various other lengths and sequence composition may also be used.

The invention also includes oligonucleotides encoding the peptide linkers of the invention. Such oligonucleotides should be "fused in frame" with the polynucleotides encoding the IgE-binding domain and HSA component, and preferably include restriction sites unique in the molecule. By "fused in frame" is meant that:

(1) there is no shift in reading frame of the IgE-binding domain or the HSA component caused by the linker oligonucleotide; and (2) there is no translation termination between the reading frames of the IgE-binding domain and the HSA-component.

The invention further encompasses physiologically functional equivalents of the novel fusion polypeptides which are normally intermediates in the synthesis of the novel polypeptides. The term "physiologically functional equivalent" preferably refers to a larger molecule comprising the fusion polypeptide of the invention to which has been added such amino acid sequence as is necessary or desirable for effective expression and secretion of the mature recombinant fusion polypeptide of the invention from a particular host cell. Such added sequence is typically at the amino terminus of the mature polypeptide, and usually constitutes a leader (i.e. signal) sequence which serves to direct them into the secretory pathway, and is normally cleaved upon or prior to secretion of the polypeptide from the cell. The signal sequence can be derived from the natural N-terminal region of the relevant polypeptide, or it can be obtained from host genes coding for secreted proteins, or it can derive from any sequence known to increase the secretion of the polypeptide of interest, including synthetic sequences and all combinations between a "pre-" and a "pro-" region. The juncture between the signal sequence and the sequence encoding the mature polypeptide should correspond to a site of cleavage in the host.

In fusion polypeptides wherein an IgE-binding domain "leads" expression, i.e. is upstream from other coding sequences in the fusion molecule, it is expedient to utilize the leader sequence of native human FcεRIα (i.e. $Met_1$+$Ala_2$-$Ala_{25}$ of SEQ. ID. NO. 1), and this has been employed effectively to obtain the mature polypeptide from mammalian expression systems (e.g. CHO, COS), as well as from yeast (*Pichia pastoris*).

An example of a physiologically functional equivalent of the mature dimeric fusion polypeptide $IgE^R$-$L_1$-HSA II-$L_2$-$IgE^R$ is: pre- $IgE^R$-$L_1$-HSA II-$L_2$-$IgE^R$. However, the additional leader sequence is not necessarily that of human FcεRIα and may be obtained from any suitable source, provided it is suitable to effect expression/secretion of the mature polypeptide from the particular host cell. For example, the prepro- sequence of HSA may also be used to prepare the above dimeric fusion polypeptides, particularly for expression in yeast.

In fusion polypeptides of the invention wherein an HSA component leads expression, a suitable leader sequence may comprise the native leader sequences. For example, the native prepro- region of HSA may be used to accomplish secretion of the mature heterologous polypeptide from mammalian (e.g. CHO, COS) cells or yeast (*Pichia pastoris*).

An example of a physiologically functional equivalent of the mature fusion polypeptide represented by HSA II-$L_2$-$IgE^R$ is: prepro HSA II-$L_2$-$IgE^R$. However, other leader sequences, not necessarily native to HSA or to the host cell, may provide effective expression of the mature fusion protein in certain hosts (U.S. Pat. No. 5,100,784; U.S. Pat. No. 5,330,901).

The invention also comprises polynucleotides which are intermediates in the preparation of the recombinant fusion polypeptides of the invention, including polynucleotides encoding the fusion polypeptides or physiologically functional equivalents thereof and oligonucleotides encoding linker peptides, e.g. as depicted in FIG. 8.

As a further aspect, there is provided a process for preparing a recombinant fusion polypeptide as defined above or salt thereof, which comprises:
(a) transforming a host cell with a vector comprising DNA encoding a fusion polypeptide as defined above or a physiologically functional equivalent thereof;
(b) expressing the fusion polypeptide or its physiologically functional equivalent in that cell, whereby the physiologically functional equivalent polypeptide is modified (e.g. by cleavage of a signal sequence) to yield a fusion polypeptide as defined above; and
(c) recovering the resultant polypeptide from the host cell, preferably as a secreted product, optionally in the form of a salt thereof.

A still further aspect of the present invention provides vectors, preferably plasmids, for use in the expression of the fusion polypeptides. These vectors comprise DNA encoding the polynucleotides defined above or physiologically functional equivalents thereof. In general, appropriate vectors which can transform microorganisms capable of expressing the fusion polypeptides include expression vectors comprising nucleotide sequences coding for the fusion polypeptides joined to transcriptional and translational regulatory sequences, such as promoters, which together constitute an expression cassette. The promoters may derive from genes of the particular host used, or such control regions may be modified, for example, by in vitro site-directed mutagenesis, by introduction of additional control elements or synthetic sequences. The expression cassette specifically used in the present invention thus also includes a transcription and translation termination region which is functional in the intended host and which is positioned at the 3' end of the sequence functional in the intended host and which is positioned at the 3' end of the sequence encoding the hybrid macromolecule. In addition o the expression cassette, the vector will include one or several markers enabling the transformed host to be selected. Such markers include markers conferring resistance to antibiotics such as G418. These resistance genes will be placed under the control of the appropriate transcription and translation signals allowing for expression in a given host.

More particularly, the preparation of recombinant fusion polypeptides of the invention may be effected e.g. as follows:

A. Construction of Fusion Protein Expression Vectors

The first step in the construction of recombinant fusion polypeptides is to subclone portions of the fusion polypeptides in cloning vectors. In this context, a "cloning vector" is a DNA molecule, such as a plasmid, cosmid or bacteriophage, that can replicate autonomously in a host prokaryotic cell. Cloning vectors typically contain one or a small number of restriction endonuclease recognition sites at which foreign DNA sequences can be inserted in a determinable fashion without loss of an essential biological function of the vector, as well as a marker gene that is suitable for use in the identification and selection of cells transformed with the cloning vector. Marker genes typically include genes that provide tetracycline resistance or ampicillin resistance. Suitable cloning vectors are described in J. Sambrook et al. (eds.), *Molecular Cloning: A Laboratory Manual*, 2nd Edition (Cold Spring Harbor Laboratory Press [1989]) and can be obtained, for example, from various sources.

The FcεRIα cDNA clone pGEM-3-110B-1, is described in A. Shimizu et al., *Proc. Nat. Acad. Sci. USA* 85 [1988] 1907–1911 and can be obtained from the American Type Tissue Collection (ATCC stock #67566). Single-stranded human liver cDNA can be obtained from Clontech (PCR-ready Quick Clone cDNA, Cat. D#7113–1). The sequence of HSA is available from GenBank under Accession #s: VOO495, JOOO78, LOO132, LOO133. HSA cDNA can be obtained by PCR amplification using oligonucleotides #24 and 25, as described in Example 2.

A polynucleotide encoding a suitable IgE-binding domain or HSA component DNA can be prepared using the polymerase chain reaction (PCR). PCR utilizes a single-stranded cDNA template and a mixture of oligonucleotide primers. The PCR procedure is perfomed via well-known methodology (see e.g. C. R. M. Bangham, "The Polymerase Chain Reaction: Getting Started" in *Protocols in Human Molecular Genetics*, Human Press [1991], Ch.I, p. 1–8). PCR kits and material for use in the kits are also commercially available from various sources. Kits and methods for using them are further described in e.g. U.S. Pat. No. 5,487,993).

DNA sequences encoding signal peptides can be added by PCR or if necessary using synthetic oligonucleotides that encode known signal peptide sequences. DNA sequences encoding a heterologous signal peptide are subcloned in frame with DNA sequences encoding the N-terminus of the fusion polypeptide.

Fusion of the polynucleotides may be accomplished by subcloning in intermediate vectors. Alternatively, one gene can be cloned directly into a vector containing the other gene. Linkers and adapters can be used for joining the DNA sequences.

Subcloning is performed in accordance with conventional techniques, such as by use of restriction enzyme digestion to provide appropriate termini, the use of alkaline phosphatase treatment to avoid undesirable joining of DNA molecules, and ligation with appropriate ligases. Techniques for such manipulation are described in the literature and are known in the art.

B. Expression Cloning of Fusion Polyteptides

The cloned fusion protein is then cleaved from the cloning vector and inserted into an expression vector. Suitable expression vectors typically contain
(1) prokaryotic DNA elements coding for a bacterial replication origin and an antibiotic resistance marker to provide for the growth and selection of the expression vector in a bacterial host;
(2) eukaryotic DNA elements that control initiation of transcription, such as a promoter; and
(3) DNA elements that control the processing of transcripts, such as a transcription termination/polyadenylation sequence.

Therefore, another aspect of the present invention concerns vectors, preferably plasmid vectors, for use in the expression of the fusion polypeptides of the invention, which contain the polynucleotide sequences described herein which code for the fusion polypeptides of the invention. Appropriate expression vectors which can transform procaryotic or eucaryotic cells include expression vectors comprising nucleotide sequences coding for the fusion molecules joined to transcriptional and translational regulatory sequences which are selected according to the host cells used. For expression in *E. coli*, vectors such as that described by M. W. Robertson, *J. Biol. Chem.* 268 [1993] 12736–12743 can be used. The product is expected to be disulfide-bonded, but not glycosylated. For expression in yeast, an expression vector such as pHIL-D2 supplied with the Invitrogen (San Diego, Calif., USA) *Pichia* pastoris expression kit (catalogue #K1710-01) can be used. The protein product is expected to be disulfide-bonded and glycosylated. Other suitable yeast expression systems include *Saccharomyces cerevisiae* and *Kluveromyces lactis*. For expression in baculovirus, vectors such as pAC360, pVL1392 and pL1393 (Invitrogen, San Diego, Calif., USA) are useful for infection of insect cells, which would be expected to secrete a glycosylated and disulfide-bonded product.

A The fusion polypeptide of the invention normally is a glycoprotein, particularly when expressed in mammalian cells, and the invention includes fusion polypeptides in any glycosylation, or disulfide bridging, state. In particular, mutational analysis suggests that N-linked glycosylation at the first, second and seventh positions of the N-linked glycosylation sites of the $IgE^R$ receptor a chain (A. Shimizu et al., *PNAS USA* 85 [1988] 1907–1911, FIG. 2) (corresponding to amino acid residues 46, 67 and 191 of SEQ. ID. NO. 1), promotes biological activity of the $IgE^R$ molecule and monomers and dimers comprising it. The most preferred expression system is one in which any sugars added will be most similar to those in the native molecule from which the polypeptide is derived. Yeast and insect cells are known to modify glycoproteins differently from mammalian cells, whereas *E. coli* does not add sugar molecules after secretion. Therefore, while expression from any of these expression systems can yield a protein product which is useful for diagnostic applications (for example, the detection of an allergic condition), the most preferred form for expressing this product for use as a therapeutic molecule is expression in mammalian cells or possibly expression in the milk of transgenic mammals.

For expression in a mammalian host, the transcriptional and translational regulatory signals used in an expression cassette may be derived from viral sources, such as adenovirus, bovine papilloma virus or simian virus, in which the regulatory signals are associated with a particular gene which has a high level of expression. Suitable transcriptional and translational regulatory sequences also can be obtained from mammalian genes, such as actin, collagen, myosin, and metallothionein genes. Transcriptional regulatory sequences include a promoter region sufficient to direct the initiation of RNA synthesis in a mammalian cell. Examples of typical mammalian cells are Chinese hamster ovary (CHO) cells, SV40-transformed monkey kidney cells (COS), HeLa, BHK, NIH Swiss mouse embryo cells, rat, monkey or human fibroblasts, or rat hepatoma cells.

For expression in mammalian cells, the preferred method is secretion from CHO cells. Neither CHO nor human cells add the α1,3-linked galactose residues which are typical of expression in murine cells such as C127 and SP2/0 cells. Antibodies to this sugar linkage are present in human serum [C. F. Goochee et al., *BioTechnol.* 9 [1991] 1347–1355] and can affect the half-life, accessibility and clearance of recombinant products expressed from these murine cells. CHO, dhfr- cells are mutant for dihydrofolate reductase (DHFR), and therefore are unable to synthesize purines, thymidine and glycine de novo. The copy number of chromosomally integrated plasmids bearing wild type copies of the DHFR gene can be increased or amplified by exposing cells transformed with these plasmids to increasing levels of methotrexate, a folate analogue which competes for folate binding at the active site of the enzyme. A suitable vector for expression in CHO, dhfr- cells is pMT2 (R. J. Kaufman et al. *EMBO J.* 6 [1987] 187–193)]. The pMT2 vector has a wild type copy of the DHFR gene which is transcribed as a single mRNA with the foreign gene. Therefore, upon treatment of transformed CHO, dhfr- cells with increasing concentrations of methotrexate, both the foreign gene and the DHFR gene are co-amplified. The product secreted from these cells is expected to be disulfide-bonded and glycosylated in a mammalian pattern.

An expression vector can be introduced into host cells using a variety of techniques including calcium phosphate transfection, liposome-mediated transfection, electroporation, and the like. Preferably, transfected cells are selected and propagated wherein the expression vector is stably integrated in the host cell genome to produce stable transformants. The cells can be cultured, for example, in DMEM media. The polypeptide secreted into the media can be recovered by standard biochemical approaches following transient expression 24–72 hours after transfection of the cells or after establishment of stable cell lines following selection by e.g. antibiotic resistance.

Conventional methods for recovering an expressed polypeptide from a culture include fractionation of the polypeptide-containing portion of the culture using well known biochemical techniques. For instance, the methods of gel filtration, gel chromatography, ultrafiltration, electrophoresis, ion exchange or affinity chromatography, such as are known for protein fractionations, can be used to isolate the expressed proteins found in the culture. In addition, conventional immunochemical methods, such as immunoaffinity or immunoabsorption can be performed. Techniques for transformation, culture, amplification, screening and product production and purification are also well-known (see e.g. J. Sambrook et al. [1989], supra; R. J. Kaufman, *Genetic Engineering: Principles and Methods*, Plenum Press, Vol. 9 [1987] 156–198).

The fusion polypeptides of the invention are indicated for use therapeutically to treat mammalian, and in particular, human, patients suffering from allergies. The IgE-binding domain of the fusion polypeptides competes for IgE with the IgE receptor naturally present on mast cells, basophils and Langerhans cells, so that IgE is bound to the administered protein and unable to bind to these allergy effector cells to mediate the allergic response. The IgE-binding domain also competes with the $IgE^R$ receptor, FcεRI, by binding to auto-antibodies to FcεRI.

Therefore the present invention provides a pharmaceutical composition for competitively binding IgE (and/or autoantibodies to FcεRI), and/or inhibiting production of IgE, and thus for suppressive and/or preventative treatment of IgE- or IgE-receptor- mediated disorders, and more specifically, allergy and conditions associated with allergy, such as atopic dermatitis, atopic asthma and chronic urticaria.

By "IgE- or IgE receptor- mediated disorders" is meant disorders associated with the binding of the cell-bound IgE receptor, FcεRI, to IgE or to auto-antibodies to FcεRI, e.g. type I allergic reactions ("hyper-IgE syndrome") such as bronchial asthma, atopic asthma, hay fever, pollen allergy, allergic rhinitis, atopic dermatitis, eczema, anaphylaxis, as well as chronic urticaria, and also non-allergic Kimura's disease, and other pulmonary, dermatological or autoimmune diseases.

In particular, atopic dermatitis, one of the most dramatic manifestations of atopy, is a chronic inflammatory skin disease associated with high serum IgE levels and a sensitization to various environmental allergens (M.-A. Morren et al., *J. Am. Acad. Dermatol.* 31 [1994] 467–473). Current treatment of atopic dermatitis concentrates on the use of steroid-containing creams, and severe cases of atopic dermatitis have been successfully treated with cyclosporin A (H. Granlund et al., *Br. J. Dermatol.* 132 [1995] 106–112), but the side effects restrict this treatment to a minority of the patients. An agent that inhibits the functions of IgE such as mast cell degranulation and IgE-mediated antigen presentation by B cells and other antigen presenting cells would be superior to any presently known treatment of atopic dermatitis and in addition also be useful for other milder forms of allergy.

In addition to atopic dermatitis and atopic asthma, the polypeptides of the invention can be used to treat or prevent chronic urticaria (CU), in which mast cell degranulation through activation of FcϵRIα plays a role. The fusion polypeptides of the invention can clear circulating autoantibodies against FcϵRIα, in contrast to anti-IgE monoclonal antibodies alternatively proposed for treatment of the disease.

The polypeptides may be administered in the form of a pharmaceutical composition comprising a polypeptide of the invention, preferably an unmodified polypeptide, or a pharmaceutically acceptable salt thereof, in a pharmaceutically acceptable carrier or diluent.

The term "salt" refers in particular to pharmaceutically acceptable salts prepared from pharmaceutically acceptable, non-toxic acids to form acid addition salts of e.g. an amino group of the polypeptide chain, or from pharmaceutically acceptable non-toxic bases to form basic salts of e.g. a carboxyl group of the polypeptide chain. Such salts may be formed as internal salts and/or as salts of the amino or carboxylic acid terminus of the polypeptide of the invention.

Suitable pharmaceutically acceptable acid addition salts are those of pharmaceutically acceptable, non-toxic organic acids, polymeric acids, or inorganic acids. Examples of suitable organic acids comprise acetic, ascorbic, benzoic, benzenesulfonic, citric. ethanesulfonic, fumaric, gluconic, glutamic, hydrobromic, hydrochloric, isothionic, lactic, maleic, malic, mandelic, methanesulfonic, mucic, nitric, oxalic, pamoic, pantothenic, phosphoric, salicylic, succinic, sulfuric, tartaric and p-toluenesulfonic, as well as polymeric acids such as tannic acid or carboxymethyl cellulose. Suitable inorganic acids include mineral acids such as hydrochloric, hydrobromic, sulfuric, phosphoric and nitric acid.

Examples of suitable inorganic bases for forming salts of a carboxyl group include the alkali metal salts such as sodium, potassium and lithium salts; the alkaline earth salts such as calcium, barium and magnesium salts; and ammonium, copper, ferrous, ferric, zinc, manganous, aluminum and manganic salts. Preferred are the ammonium, calcium, magnesium, potassium, and sodium salts. Examples of pharmaceutically acceptable organic bases suitable for forming salts of a carboxyl group include organic amines, such as trimethylamine, triethylamine, tri (n-propyl)amine, dicyclohexylamine, β-(dimethylamino) ethanol, tris(hydroxymethyl)aminomethane, triethanolamine, β-(diethylamino)ethanol, arginine, lysine, histidien, N-ethylpiperidine, hydrabamine, choline, betaine, ethylenediamine, glucosamine, methylglucamnine, theobromine, purines, piperazines, piperidines, caffeine and procaine.

Acid addition salts of the polypeptides may be prepared in conventional manner by contacting the polypeptide with one or more equivalents of the desired inorganic or organic acid such as hydrochloric acid. Salts of carboxyl groups of the peptide may be conventionally prepared by contacting the peptide with one or more equivalents of a desired base such as a metallic hydroxide base, e.g. sodium hydroxide; a metal carbonate or bicarbonate base such as sodium carbonate or sodium bicarbonate; or an amine base such as triethylamine or triethanolamine.

The invention thus also concerns pharmaceutical compositions comprising a novel fusion polypeptide as defined above or a pharmaceutically acceptable salt thereof, together with a pharmaceutically acceptable carrier or diluent. The carrier is preferably a sterile, pyrogen-free, parenterally acceptable liquid. Water, physiological saline, aqueous dextrose, and glycols are preferred liquid carriers or diluents, particularly (when isotonic) for injectable solutions. The composition may be a conventionally prepared lyophilizate.

The compositions can be administered systemically, i.e. parenterally (e.g. intramuscularly, intravenously, subcutaneously or intradermally), or by intraperitoneal administration. For parenteral administration, it is preferred that the fusion polypeptides be essentially soluble in patient serum or plasma, e.g. that at least 1 milligram of polypeptide is soluble in one mililiter of serum or plasma.

The compositions can also be administered by known techniques for topical administration. Examples of suitable dosage forms include sprays, opthalmic solutions, nasal solutions and ointments. For example, a spray can be manufactured by dissolving the peptide in an appropriate solvent and putting it in a spray to serve as an aerosol for commonly employed inhalation therapy. An opthalmic or nasal solution can be manufactured by dissolving the active ingredient in distilled water, adding any auxiliary agent required, such as a buffer, isotonizing agent, thickener, preservative, stabilizer, surfactant or antiseptic, adjusting the mixture to pH 4 to 9. Ointments can be obtained e.g. by preparing a composition from a polymer solution, such as 2% aqueous carboxyvinyl polymer, and a base, such as 2% sodium hydroxide, mixing to obtain a gel, and mixing with the gel an amount of purified fusion polypeptide.

The composition is preferably admirnistered subcutaneously or intravenously, and most typically, subcutaneously.

The invention also comprises a method of treatment of allergic conditions comprising administration of a therapeutically effective amount of a fusion polypeptide of the invention or a pharmaceutically acceptable salt thereof to a patient in need of such treatment. The method of treatment is practiced during the course of an allergic disease state (i.e. when the relief of symptoms is specifically required); or as a continuous or prophylactic treatment (i.e. prior to the onset of an anticipated IgE- or IgE-receptor- mediated disorder, such as an allergic reaction).

The effective dosage in accordance herewith can vary over a wide range taking into consideration e.g. the degree or severity of the condition being treated, the age, sex and condition of the subject, the length of treatment, and the potency of the particular fusion protein. factors which are determinable by conventional methods.

Since individual subjects widely vary in their IgE (as well as antibody to FcϵRI) content. a therapeutically effective dosage in accordance herewith can best be described as being between $5 \times 10^2$ and $1 \times 10^4$ times the total content of serum IgE and antibodies to FcϵRI. on a molar scale. The patient may be treated on a daily basis in single or multiple administration. The composition may also be administered on a per month basis (or at such weekly intervals as may be appropriate), also in either single or multiple administrations.

For an average subject (70 kg), a suitable monthly dosage can range from a lower dosage of about 0.5 mg per month to an upper dosage of about 500 mg per month, preferably of from about 1 mg to about 300 mg, more preferably of from about 20 mg to about 250 mg, per month, of the fusion polypeptide of the invention, such as the dimer of Example 7, conveniently administered in divided dosages once or twice a month. Higher dosage ranges, e.g. 500 mg per month to 2 g per month, may be indicated in patients having high serum IgE concentrations or in early treatment phases.

The dosage and timing of administration may vary. Initial administrations of the composition may be at higher dosages within the above ranges, and administered more frequently than administrations later in the treatment of the disease. Appropriate dosages may be determined by measuring the content of IgE and antibodies to FcεRI in the patient's serum, as indicated above. For example, early in the course of disease, the fusion polypeptide of the invention, such as the dimer of Example 7, may be administered in weekly doses of 200–500 mg of polypeptide in the average patient (70 kg). After clearance of serum IgE and antibody to FcεRI, the treatment regimen may be reduced to weekly treatments or treatments every other week, with dosages ranging from 50 μg to 100 mg of polypeptide per treatment.

The compositions of the present invention can be administered either alone or in combination with other compounds of the present invention or further pharmaceutical agents such as antihistamines or corticosteroids.

The invention also comprises the use of the fusion polypeptides of the invention in an in vitro diagnostic assay of any standard format, e.g. ELISA, to determine the level of IgE or auto-antibodies to FcεRI (e.g. in chronic urticaria patients) in a biological sample obtained from a human patient, e.g. blood or tissue samples. The HSA component advantageously facilitates binding and detection of IgE or autoantibodies to FcεRI in an ELISA formatted assay. The amount of IgE or auto-antibodies present in the sample can serve as a measure of the allergic response of the patient to a substance to which the patient has been exposed. IgE or auto-antibody levels can also be measured to determine the efficiency of anti-allergy therapies, and to monitor a patient's allergic status over time.

The invention further comprises a method of performing gene therapy in humans using a polynucleotide encoding a fusion polypeptide of the invention, for treatment of IgE- or IgE receptor- mediated disorders. The gene therapy method comprises modifying cells of a patient by introducing therein a polynucleotide encoding a fusion polypeptide of the invention and expressing the polypeptide from such cells. For example, somatic cells may first be removed from a patient, then genetically modified in culture by insertion of the polynucleotide, and the resultant modified cells reintroduced into the patient, whereby a polypeptide of the invention is expressed by the cells of the patient.

Alternatively, the cells may be modified in vivo by direct insertion of vector DNA encoding the polypeptide.

Suitable cells for modification include endothelial cells or leukocytes. For gene therapy applications the polynucleotide of the invention is preferably under the control of a regulable (e.g. inducible) promoter. Expression of the polypeptide may thereby be made dependent on exposure of the patient to an exogenous factor using known regulable promoter systems.

The invention also includes utilizing the methods of gene therapy to prepare non-human somatic recombinant or transgenic animals expressing the fusion polypeptides of the invention, e.g. into milk. Such modified non-human animals also form part of the invention. Examples of useful animals include mnice, rats, rabbits, pigs, sheep, goats and cattle, all of which have been made transgenic using standard techniques (e.g., D. R. Hurwitz et al., Transgenic Research 3 [1994] 365–375). The animals may be used for modelling purposes or actual production of a protein. In particular, the invention concerns a transgenic mouse, goat, cow or pig expressing a fusion polypeptide of the invention. Methods for making such animals are well known. A polynucleotide encoding the fusion protein of the invention can be introduced into the somatic cells of the animals, in vitro or in vivo, to produce somatic recombinant animals which are modified genetically but which cannot pass the genetic modification on to offspring. Alternatively, the polynucleotide can be inserted into cells of embryos for production of transgenic animals able to pass on the capability of expressing the proteins of the invention to offspring.

Transfection of cells for gene therapy can be accomplished in conventional manner, e.g. by electroporation, calcium phosphate precipitation, a lipofectin-based procedure, intramuscular injection, microinjection or through use of a "gene gun." Plasmid-based vectors preferably contain a marker such as the neomycin gene for selection of stable transfectants with the cytotoxic aminoglycoside G418 in eukaryotic cells.

Infection is accomplished by incorporating the genetic sequence for the fusion polypeptide into a retroviral vector. Various procedures are known in the art for such incorporation. One such procedure which has been widely used employs a defective murine retrovirus for packaging the retrovirus, and an amphotropic packaging cell line to prepare infectious amphotropic virus for use in infecting the target donor cells.

Provisional Application No. 60/022,689 filed Jul. 26, 1996, from which this application claims benefit, is hereby incorporated by reference in its entirety.

Further characterization may be effected eg. as follows:

In vivo Determination of Serum Half Life
General Procedure:

Female SKH1/hr/hr Charles River mice weighing approximately 25 g are injected intravenously with test proteins diluted in sterile $Ca^{+2}$, $Mg^{2+}$ free PBS. The mice are divided into groups as follows:

Group (i) receiving 130 μg (1 nmole) of fusion polypeptide, e.g. the dimer $IgE^R$-$L_1$-HSA II-$L_2$-IgE prepared as in Example 7, or Group (ii) receiving 60 μg $IgE^R$ (2 nmoles), or Group (iii) receiving 65 μg HSA I (1 nmole).

100 μl of blood are taken from each mouse at 10 minutes, 30 minutes, 3 hours, 6 hours and 12 hours after injection. Serum is prepared by centrifugation. Serum concentration levels of the various protiens are determined by a) IgE receptor ELISA binding assay. b) inhibition ELISA; or c) HSA Sandwich ELISA, as follows:

a) $IgR^R$ ELISA Binding Assay:

IgE serum concentration is determined by detection of IgE binding by the following Sandwich ELISA: 200 ng human IgE is immobilized in COSTAR Strip Plate-8 wells (Cambridge. Mass., USA) in 100 μl coating buffer in a humidifed chamber at 4° C. overnight. Each well is washed twice with 300 μl $Ca^{2+}$, $Mg^{2+}$-free PBS, pH 7.2. The plates are blocked for one hour at room temperature with 200 μl $Ca^{2+}$, $Mg^{2+}$+-free PBS containing 5%1 BSA (Sigma). After washing twice with 300 μl $Ca^{2+}$, $Mg^{2+}$-free PBS containing 0.05% Tween 20 (PBST), samples diluted in 100 μl of 1:10 diluted (in $Ca^{2+}$, $Mg^{2+}$-free PBS) mouse serum are added and incubated for one hour at room temperature.

The wells are washed twice with 300 μl PBS and incubated with 100 μl (1ng) of a monoclonal anti-human IgE receptor antibody such as 5H5/F8 for one hour at room temperature. Again, the wells are washed twice with 300 μl PBST and incubated with 100 μl of goat anti-mouse IgG- HRP (Biorad, 1:2000 diluted in $Ca^{2+}$, $Mg^{2+}$ free PBS) for 1 hour at room temperature. Plates were washed three times with 300 µl of PBST, and horse radish peroxidase (HRP) conjugates are detected with 100 µl of ABTS (Biorad) substrate. The reaction is stopped after 5 minutes with 100 µl of 3% oxalic acid. Color intensities are measured with an EASY READER photometer at 405 nm.

b) Inhibition ELISA:

100 ng FcεRIα is immobilized in Nunc 96 well Immunoplates (F 96 cert. Maxisorb) in 100 µl coating buffer (0.1 M $NaHCO_3$, 0.01% $NaN_3$ pH:9.6) in a humidified chamber at 4° C. overnight. Each well is washed 4 times with 300 µl PBS, 0.05% Tween 20 (washing buffer). To different sets of wells, either a negative control (50 µl of mouse serum diluted 1:25 in PBS, 0.05% Tween 20, 2% FCS), a dilution series of the fusion polypeptide standard, e.g. $IgE^R$-$L_1$-HSAII-$L_2$-$IgE^R$ standard (dilutions from 400 ng/ml to 1.6 ng/ml) or dilution series of the samples are added. The standard and the samples are diluted in mouse serum diluted 1:25 in PBS, 0.05% Tween 20, 2% FCS. Immediately afterwards 50 µl of 400 ng/µl of human IgE-Biotin conjugate in dilution buffer is added and mixed. The final mouse serum dilution in the incubation mixture is 1:50.

After incubation for two hours at 37° C., the plates are washed 4 times with 300 µl washing buffer, and 50 µl steptavidine-alkaline phosphatase conjugate (Gibco) diluted 1:1000 in dilution buffer is added and incubated for one hour at 37° C. The plates are washed 4 times with 300 µl washing buffer and after addition of 100 µl substrate (1 mg/ml p-nitrophenyl-phosphate in diethanolamine buffer, pH 9.8 [BIORAD]) the reaction is stopped after incubation for 30 minutes at 37° C. with 50 µl of 2 M NaOH. Optical densities are measured with a BIOMEK-1000 workstation photometer at 405 nm. The quantitative evaluation from the standard curves (4-parameter logistic curve fitting) is made with the Beckman IMMUNOFIT ELISA evaluation program.

Calculation:

% binding=[OD (sample or standard value)/OD (buffer value)]× 100 c) HSA Sandwich ELISA:

500 ng monoclonal anti-mouse HSA (HSA-9) is immobilized in Nunc 96 well Immunoplates (F96 cert. Maxisorb) in 100 µl coating buffer (0.1 M $NaHCO_3$, 0.01% $NaN_3$ pH:9.6) in a humidified chamber at 4° C. overnight. Each well is washed 4 times with 300 µl washing buffer (PBS, 0.05% Tween 20). 100 µl of 1:100 diluted mouse serum (PBS, 0.05% Tween 20, 2% FCS=dilution buffer) as negative control, or 100 µl standard (1 µg/ml–2 ng/ml human serum albumin, KABI) or 100 µl of sample diluted in 1:100 diluted mouse serum is added. After incubation for two hours at 37° C., the plates are washed 4 times with 300 µl washing buffer, and 100 µl of 1 ng/µl rabbit anti-HSA-Biotin conjugate diluted in dilution buffer is added. The anti-HSA-Biotin conjugate is purified by immunoaffinity chromatography with CH-Seph4B-HSA, and cross reactivities with mouse serum are removed by immunosorbtion with mouse serum-agarose. After incubation for two hours at 37° C., the plates are washed 4 times with 300 µl washing buffer, and 50 µl streptavidin-alkaline phosphatase conjugate (Gibco) diluted 1:1000 in dilution buffer is added and incubated for one hour at 37° C. The plates are washed 4 times with 300 µl washing buffer and after addition of 100 µl substrate (1mg/ml p-nitrophenylphosphate in diethanolamine buffer, pH 9.8, BIO-RAD), the reaction is stopped after incubation for 15 minutes at 37° C. with 50 µl 2M NaOH. Optical densities are measured with a BIOMEK-1000 workstation photometer at 405 nm. The quantitative evaluation from the standard curve (4-parameter logistic curve fitting) is made with the Beckman IMMUNOFIT ELISA evaluation program.

Figure 1A:
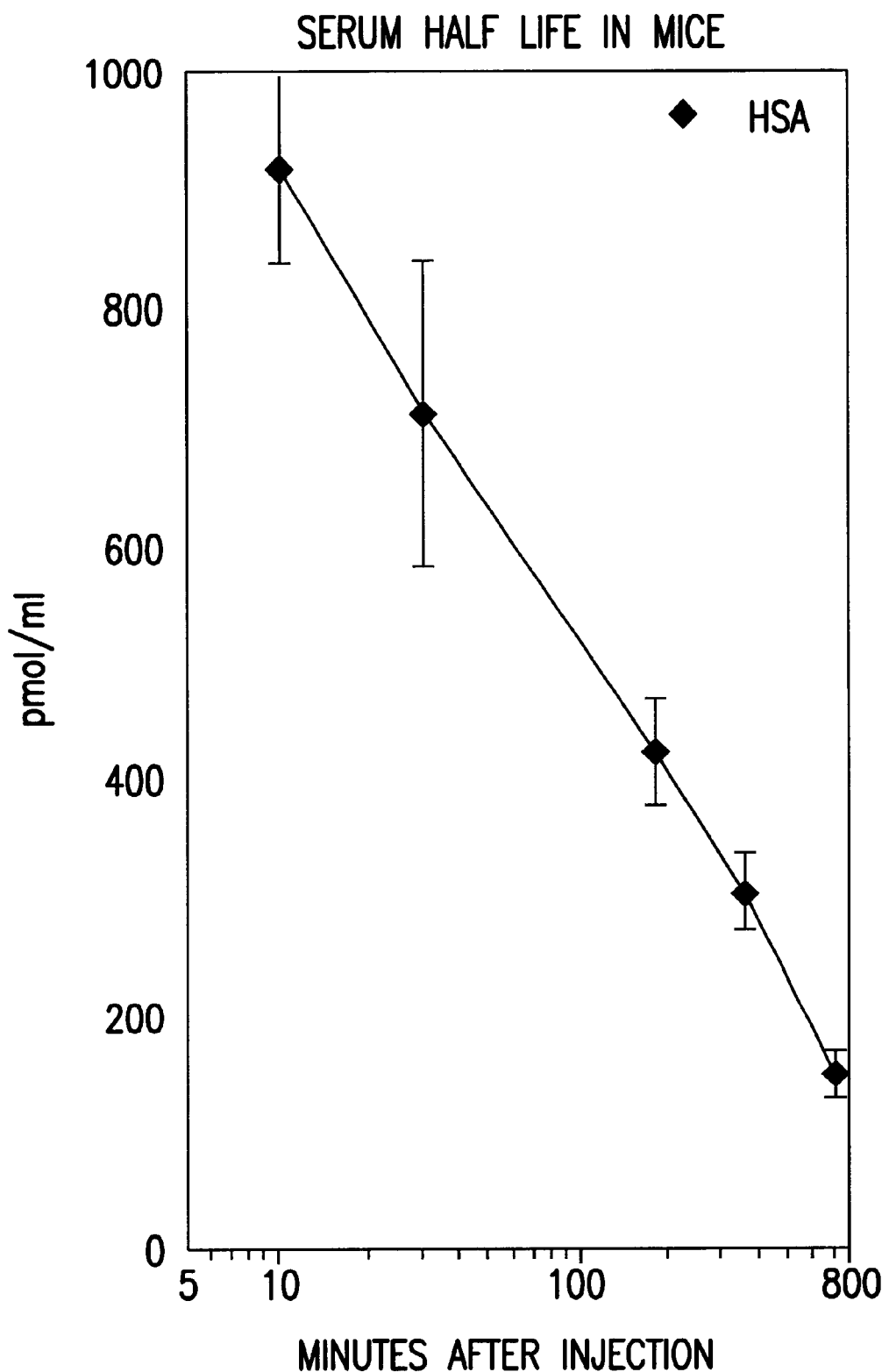
FIGS. 1A–C: Serum half life in mice: Protein concentration in vivo (in picomoles of protein per ml of serum) over time (10–800 minutes after injection) of (A) free HSA I protein, and (B) IgE$^R$ protein (referred to as "Free alpha chain") and IgE$^R$-L$_1$-HSA II-L$_2$-IgE$^R$ dimeric fusion polypeptide (referred to as "IgE$^R$-HSA-IgE$^R$" dimer) prepared from CHO cells as described in Example 7.

Results:

Concentrations for the dimeric fusion polypeptide, $IgE^R$-$L_1$-HSA II-$L_2$-$IgE^R$, the free $IgE^R$ (referred to as "free alpha chain") or HSA I (referred to as "HSA") as a function of elapsed time after injection, are given in pmoles/ml serum in FIG. 1(A) and (B).

Figure 1B:
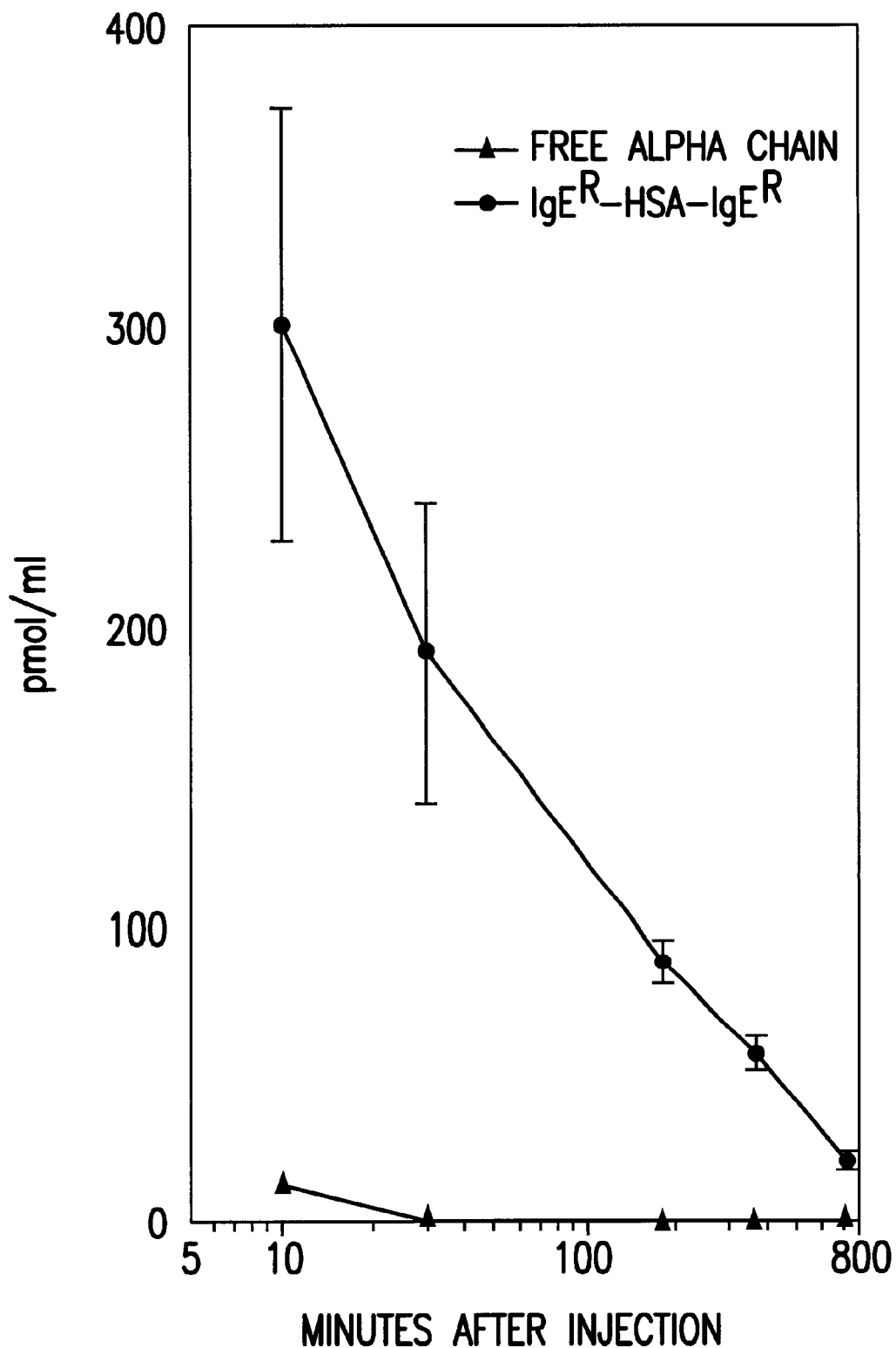

A FIG. 1(B) shows that the free receptor is only detectable in mouse serum for about 10 minutes. whereas the dimeric fusion polypeptide is still detectable about 12 hours after administration.

Figure 1C:
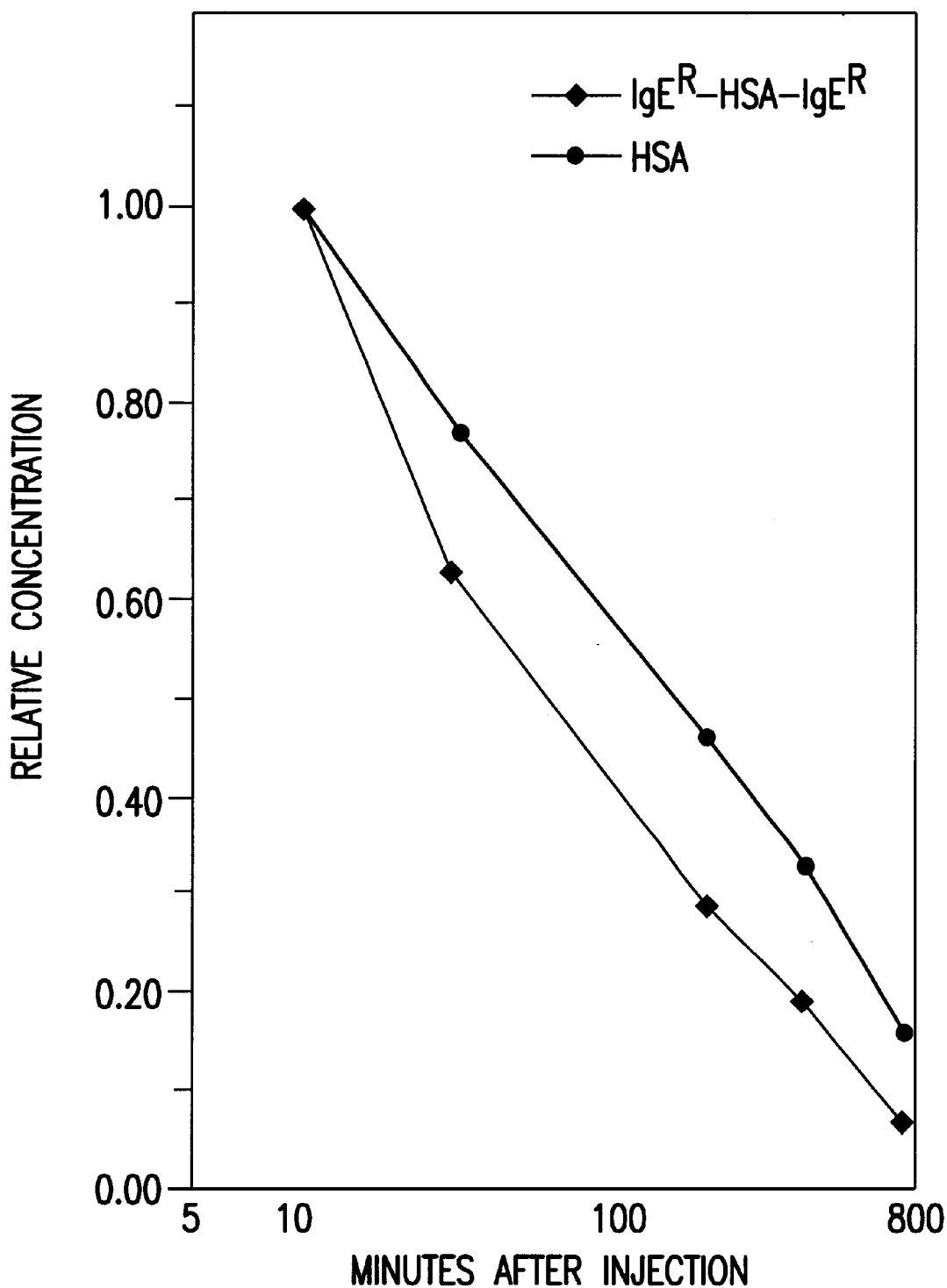

FIG. 1(C) shows the relative clearance kinetics for HSA and the dimeric fusion polypeptide. After stabilization of tissue-blood distribution in the first 10 minutes, the dimer and HSA show an almost identical clearance curve. This confirms that the serum half life of an IgE-binding domain can be substantially prolonged by fusion to HSA.

Inhibition of passive cutaneous anaphylaxis (PCA) in mice

General Procedure:

(a) Administration of Polypeptide:

Serial dilutions of 10, 50 or 500 µg/kg of fusion polypeptide, e.g. $IgE^R$-$L_1$-HSA II-$L_2$-$IgE^R$ obtained from CHO cells in Example 7, are intravenously injected into female SKH1/hr/hr Charles River mice weighing approximately 25 g at varying intervals prior to sensitization.

Three groups of mice are established depending on the amount of polypeptide injected prior to sensitization (i.e. 10 µg/kg, 50 µg/kg or 500 µg/kg). A fourth group of control mice receive 200 µg/kg PBS intravenously instead of polypeptide. The four groups of mice are each divided into three sub-groups, which differ by the interval between intravenous injection of the compound and intracutaneous sensitization with IgE [step (b) below]. The tested intervals are: 5 minutes, 15 minutes and 30 minutes.

(b) Intracutaneous Sensitization:

The mice are anaesthetized and sensitized into the back skin by 4 intradermal injections of 5 ng each monoclonal mouse anti-dinitrophenyl (DNP) IgE antibody in 10 ml PBS (BioMakor, Rehovot, Israel). In the control group, saline is injected intradermally in one site.

(c) Allergen Challenge:

90 minutes after sensitization, the mice are anesthesized again and challenged by intravenous injection of a solution containing 50 µg of dinitrophenyl-bovine serum albumin (DNP-BSA) (Calbiochem-Behring, San Diego, USA) containing 1% Evans blue. The PCA response was quantified by measuring the diameter of the stained test site due to extravasation.

Results:

These are depicted in the bar graph in FIG. 2 for the mature fusion polypeptide of Example 7 (amino acids $Val_{26}$-$Leu_{978}$ of SEQ. ID. NO. 3). At a concentration of 500 µg/kg, the dimeric fusion polypeptide completely blocks PCA at all time points of application. At 50 µg/k, treatment at 30 minutes prior to challenge gives a statistically significant reduction of 36%. At 15 minutes prior to challenge, a trend is seen with administration of both 10 and 50 µg/kg of dimer. Thus, the dimeric fusion polypeptide is efficacious in preventing PCA.

The procedures and techniques for carrying out the present invention are known in the art. Insofar as their preparation is not particularly described herein, the compounds, reagents, vectors, cell-lines, etc. to be used are known and readily available or may be obtained in conventional manner from known and readily available materials, or equivalent materials may be prepared in conventional manner from known and readily available materials.

The following non-limitative Examples illustrate the invention. All temperatures are in degrees Centigrade.

Materials and methods

PCR Amplification:

De novo chemical synthesis of the primers of the invention can be conducted using any suitable method, such as, for example, the phosphotriester or phosphodiester methods.

Methods and systems for amplifying a specific nucleic acid sequence are described in U.S. Pat. No. 4,683,195 and U.S. Pat. No. 4,683,202; and in Polymerase Chain Reaction, H. A. Erlich et al., Eds., Cold Spring Harbor Laboratory Press [1989].

Following PCR, the DNA fragments are excised and purified using the QiaEx protocol (Qiagen, Inc., Chatsworth, Calif., USA), then subcloned into a TA vector [TA Cloning® Kit (Invitrogen) (product literature, Version 2.2)]. The primers used in generating PCR amplified nucleic acids are set forth in FIG. 8. DNA is sequenced using the Sequenase method (USB, Cleveland, Ohio, USA).

Plasmids and Reagents:

The FcεRIα cDNA clone, pGEM-3-110B-1 (A. Shirnizu et al., Proc. Nat. Acad. Sci. USA 85 [1988] 1907–1911) is obtained from the American Type Tissue Collection (ATCC stock #67566). Single-stranded human liver cDNA is obtained from Clontech (PCR-ready Quick Clone cDNA, Cat. D#7113-1). The sequence of HSA is available under GenBank Accession #s VO0495, JO0078, L00132 and L00133. Restriction enzymes are obtained from Boehringer-Mannheim or Gibco/BRL. Taq DNA polymerase is obtained from Perkin-Elmer Cetus (PECI) or from Boehringer-Mannheim. The SK vector is obtained from Stratagene.

pHIL-D2 is available from Invitrogen (San Diego, Calif., USA; Catalog no. K1710-01 [1994]) (see "Pichia Expression Kit—Protein Expression—A Manual of Methods for Expression of Recombinant Proteins in Pichia pastoris— Version 3.0" [December 1994]) (hereinafter referred to as the "Invitrogen Manual").

The pXMT3 vector is derived from pMT2 (Sambrook et al. (Eds.) 1989 supra) by cloning the PstI to EcoRI linker from pUC8 (Pharmacia) into the PstI and EcoRI sites of pMT2 (R. J. Kaufman et al. [1987] supra).

Standard techniques as used below are described in Sambrook et al. (Eds.) [19891] supra.

EXAMPLE

TA Cloning Vector

Plasmid pCR2 is ligated separately with each of the PCR amplification products obtained in Examples 1 and 2. The ligation reactions are performed using T4 DNA ligase in the following reaction mixture:

25 mM Tris-HCl (pH 7.8)
10 mM $MgCl_2$
1 mM DTT
1mM ATP
50 ng vector DNA
100–200 ng PCR reaction products (unpurified)
4 units T4 DNA ligase (New England Biolabs)

Each reaction mixture is maintained at 15° for 18 hours before being transformed into competent cells.

EXAMPLE 1

PCR Amplification and Cloning of FcεRIα cDNA

FcεRIα cDNA is purified from pGEM-3-110B-1 using the Qiagen method. Then:

(A) For preparing an HSA-leading construct, PCR amplification of FcεRIα cDNA is carried out with oligonucleotides #18 and #19 (FIGS. 4, 8) using the following reaction mixture:

1 µl (50 ng) of FcεRIα cDNA;
50 pmoles of each of oligonucleotides #18 and #19
5 µl 10x PCR buffer (PECI)
0.5 µl 20 mM dNTP stock solution=200 µM final dNTPs concentration
0.5 µl (2.5 U) Taq DNA polymerase (PECI)
water to 50 µl.

The reaction mixture is overlaid with mineral oil to prevent evaporation, and thermocycled in a Perkin Elmer Cetus DNA thermocycler model 480. Cycling conditions for this reaction are: heat to 95° for 5 minutes, then 30 cycles of 94° for 1.5 minutes, 53° for 2 minutes, 72° for 3 minutes, followed by a three minute extension at 72° and an overnight soak at 4°.

Following electrophoresis an amplified product of ~550 bp is confirmed by ethidium bromide staining. The fragment is subcloned into PCR2 vector to yield pEK1 encoding $IgE^R$ (FIGS. 4, 8B).

(B) For preparing an IgE-leading construct, PCR amplification of the FcεRIα cDNA is carried out according to the procedure of (A) above except that oligonucleotides #20 and #31 (FIG. 5B) are used. Following electrophoresis on 0.7% agarose gel, an amplified product of 600 bp is confirmed by ethidium bromide staining. The fragment is subcloned into PCR2 vector to form IgER/TA#1 encoding pre-$IgE^R$ (FIG. 4)

(C) For preparing a construct encoding pre-$IgE^R$ in order to express the mature, truncated protein for use as a control in assays, PCR amplification of FcεRIα C.DNA is carried out as in (A) above with oligonucleotides #20 and #19 (FIG. 8B). Following electrophoresis, an amplified product of ~620 bp is confirmed by ethidium bromide staining. The PCR fragment is excised and subcloned into PCR II vector to provide IgERFL/TA #34, encoding pre-$IgE^R$ followed by a stop codon (FIG. 4).

EXAMPLE 2

PCR Amplification and Cloning of Human Serum Albumin cDNA

For obtaining a sequence encoding prepro-HSA II, PCR amplification of full length human serum albumin CDNA is carried out with oligonucleotides #24 and #25 (FIG. 8B), following the general procedure of Example 1(A). The resulting clone HSA/TA#1 had the sequence most closely resembling the sequence in Genbank. In this clone, seven mutations in the wobble position and one mutation which resulted in a change from lysine to glutamic acid at base 1333 were detected. The seven mutations in the wobble position were: base 309: A to T; base 744: A to G; base 795: G to A; base 951: G to A; base 1320: C to T; base 1569: A to C; base 1584: G to A (with reference to HSA/TA#1). The lysine to glutamic acid mutation was corrected back to the sequence in Genbank using site-directed mutagenesis with the oligonucleotides shown in FIG. 8A and the Bio-Rad Mutagene Phagemid in vitro mutagenesis kit (Biorad, Cat

170–3581). This method relies on the incorporation of uracil residues in the parental strand and their subsequent removal in the mutagenized strand (T. A. Kunkel, *Proc. Nat. Acad. Sci. USA* 82 [1985] 488–492). Because the point mutations in the wobble position do not alter the native amino acid sequence of the encoded protein, the above seven mutations were not corrected. Following electrophoresis, an amplified product of ~1.8 kb is confirmed by ethidium bromide staining.

The 1.8 kb product is subcloned into pCR2 vector to form HSA/TA mut #16, which is verified by DNA sequencing to contain the complete prepro-HSA II sequence. HSA/TA mut #16 is subcloned into Bluescript SK as a SpeI, HindIII fragment, yielding HSA/SK#17 (FIG. 5).

(A) For preparing an HSA-leading construct, HSAlSK#17 is digested with MstII and HindIII to remove the nucleotide sequence encoding the 3'-terminal amino acid ($Leu_{609}$); and an oligonucleotide encoding linker $L_2$, as defined above, is introduced at the 3'-terminus of the linearized HSA/SK#17 by kinasing oligonucleotides #28 and #29 (FIG. 8B) and annealing and ligating these fragments into the MstII/HindIII sites of the linearized HSA/SK#17, to yield pEK7 encoding prepro-HSA II fused to $L_2$ (FIG. 8B). Miniprep DNA is checked by BamHI digestion and by sequencing.

(B) For preparing an IgE-leading construct, HSA/SK#17 encoding prepro-HSA II is amplified by PCR with oligonucleotides #26 and #27 (FIGS. 5, 8). Oligonucleotide #26 removes the prepro sequence from HSA, and adds an oligonucleotide encoding $L_1$ at the 5 end of HSA. Oligonucleotide #27 ends at a naturally occurring, unique NcoI site at dabout nucleotide position 800 of the HSA coding sequence. PCR amplification is carried out according to the procedure in Example 1(A). An approximately 800 bp fragment isolated by gel electrophoresis and Qia is subcloned into a pCR2 vector, to provide clone HSA Nco/TA #13, the sequence of which is verified by DNA sequencing. The NcoI to NotI fragment from this clone is subcloned into cut NcoI and NotI HSA/SK#17 DNA, yielding 2 HSA/SK#5 (FIG. 5) encoding $L_1$ linked to the 5'-terminus of cDNA encoding HSA 11.

(C) For expressing HSA alone, the HSA/SK#17 construct prepared above is employed.

EXAMPLE 3

Fusion Construct HSA-IgER/SK#22 Encoding Prepro-HSA+Linker+$IgE^R$ pEK7 (containing prepro-HSA II cDNA+oligonucleotide for L2) and pEK1 (containing $IgE^R$) are digested with BamHI and SalI. The obtained 1.8 kb fragment from pEK7 is phosphatased and then ligated to the 550 Kb fragment obtained from pEK1. One positive miniprep, #23, was prepared but was contaminated with another unknown plasmid which prevented recovery of the HSA-$IgE^R$ band. Therefore, the 2.4 kb SpeI to SalI fragment containing the HSA-$IgE^R$ fusion and the 2.9 kb fragment containing the vector DNA were purified from miniprep #23 and ligated together, resulting in clone HSA - IgE/SK#49 (FIG. 9) [vector sites were found to be missing from either end of the subcloned region, and accordingly, the 2.4 kb SpeI to SalI fragment from HSA-IgE/SK#49 was subcloned into SpeI plus SalI-cut Bluescript SK, resulting in HSA-IgE/SK#22 (not shown in the Figures)].

The sequence of the junction of the HSA and linker with the IgER receptor DNA and the sequence of the ends of the fusion with the vector DNA were as expected in HSA-IgE/SK#22 as verified by DNA sequence analysis.

EXAMPLE 4

Fusion Construct IgE-HSA/SK#1 Encoding $IgE^R$+ Prepro-HSA II

Figure 10:
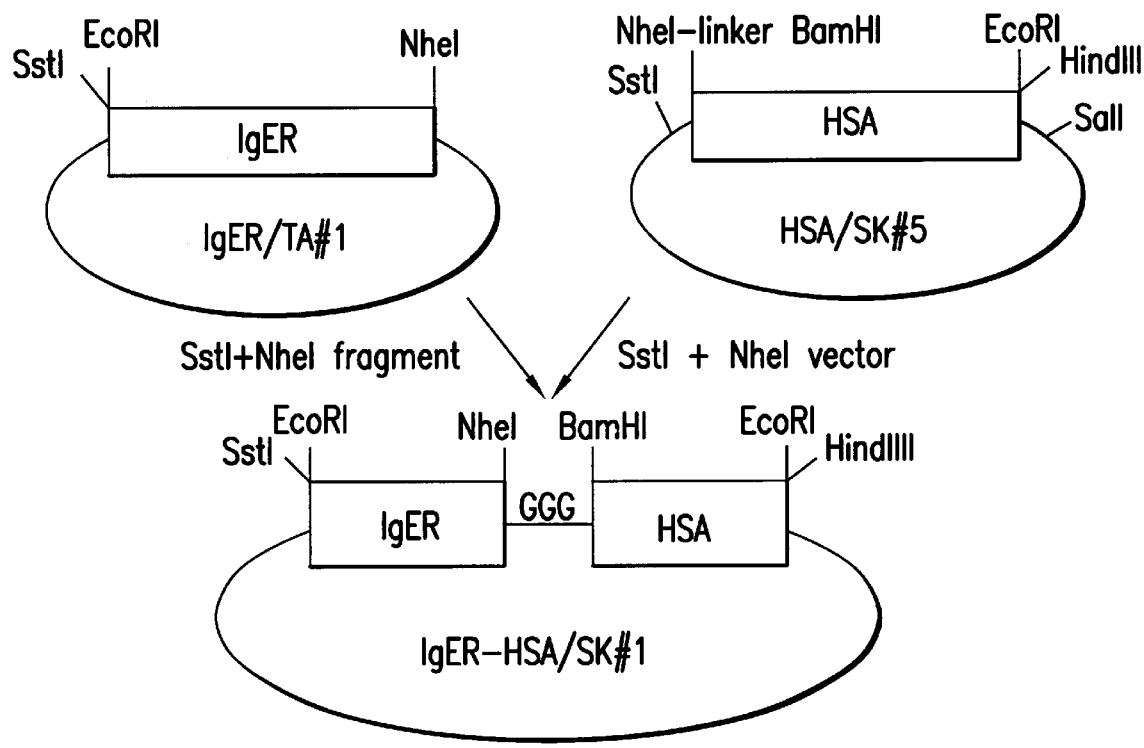

HSA/SK#5 and $IgE^R$/TA #1 are digested with SstI and NheI. The 600 bp fragment from IgE/TA #1 is purified by gel electrophoresis and ligated into the cut and phosphatase-treated HSA/SK#5, yielding clone IgE-HSA/SK#1 (FIG. 10).

EXAMPLE 5

Fusion Construct R-H-R/SK#50 Encoding Pre-$IgE^R$-$L_1$-HSA II-$L_2$-$IgE^R$

The PstI site unique to the HSA region of $IgE^R$-HSA/SK#1 and HSA-$IGE^R$/SK#49 is used to join $IgE^R$ and prepro- HSA II via the oligonucleotide for $L_2$. HSA/$IgE^R$/SK#49 and Bluescript SK are digested with PstI and SalI. A 1.2 kb fragment containing the 3' portion of HSA II, the linker and the $IgE^R$ sequence are ligated into PstI plus SalI-cut Bluescript DNA, resulting in HSA-$IgE^R$ Pst Sal/SK#37 (FIG. 11), which is digested with PstI and KpnI, and the 1.2 kb fragment is prepared.

Figure 11:
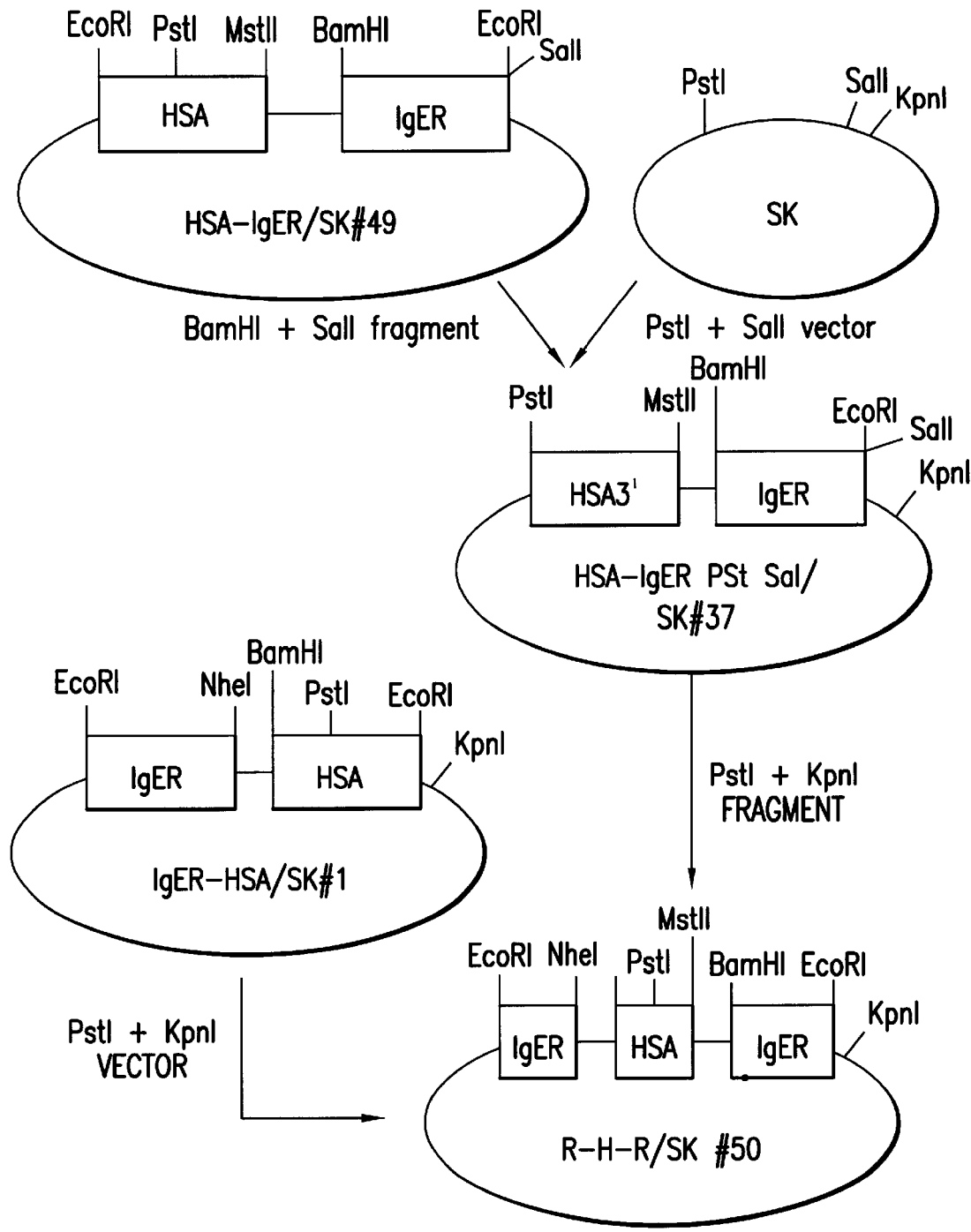

$IgE^R$-HSA/SK#1 DNA is digested with PstI and KpnI, and a 4.8 kb fragment containing the vector, $IgE^R$, linker and 5' half of HSA are isolated, phophatase-treated, and ligated to the 1.2 kb fragment from HSA-$IgE^R$ Pst Sal/SK#37. The resultant dimeric construct R-H-R/SK #50 is obtained (FIG. 11).

EXAMPLE 6

HSA II-$L_2$-$IgE^R$ Monomeric Fusion Polypeptides by Transfection and Culture of Pichia Pastoris Plasmid MB#2 encoding HSA II-$L_2$-$IgE^R$ is prepared by cutting the plasmid HSA/SK#49 with EcoRI and isolating the 2.4 kb fragment encoding the fusion protein. This fragment is ligated into the unique EcoRI site of the Pichia pastoris expression vector pHIL-D2 (Invitrogen), after digestion of plasmid pHIL-D2 with EcoRI and alkaline phosphatase treatment. The resultant MB#2 $\mu$plasmid is linearized by digestion with NotI and transformed into his4 GS 115 cells as described in the "Invitrogen Manual". His+transformants are screened for growth on methanol. Strains exhibiting slow growth on methanol are grown in minimal glycerol medium as specified in the "Invitrogen Manual" to stationary phase, transferred by centrifugation to buffered complex methanol medium and grown for 4 days. The supernatant from the cells is then assayed by ELISA for the presence of HSA and for IgE-binding ability. The IgE-binding ability of the product obtained secreted from P. pastoris was equivalent on a molar basis to the HSA concentration and fully biologically active.

EXAMPLE 7

$IgE^R$-$L_1$-HSA II-$L_2$-$IgE^R$ Dimeric Fusion Polypeptide by Transfection and Culture of CHO Cells Plasmid pXMT3-RIα-HSA-RIα (containing the polynucleotide of SEQ. ID. NO. 4 encoding pre-$IgE^R$-$L_1$-HSA II-L$_2$-IgE$^R$) is prepared by digestion of R-H-R/SK #50 (see Example 5) with EcoRI and isolation of the 3 kb EcoRI fragment encoding the dimeric fusion polypeptide. This fragment is ligated into the unique EcoRI site of pXMT3 after digestion of pXMT3 with EcoRI and alkaline phosphatase-treatment.

The plasmid is transfected into CHO DUKX B11 cells. These cells lack a functional dhfr-gene (dihydrofolate reductase) required for nucleoside synthesis. Therefore, cells are maintained in Alpha+medium (MEM ALPHA MEDIUM with ribonucleosides and deoxyribonucleosides/Gibco) containing 10% fetal calf serum (FCS). For transfection, the cells are washed twice in Ca$^{++}$-Mg$^{++}$-free PBS (CMF-PBS) and cell concentration is adjusted to 2×10$^6$ cells/ml in CMF-PBS. 0.8 ml of the cell suspension is added to 15 μg of plasmid DNA. Transfection is done by electroporation using a BIO RAD Gene Pulser (voltage=1000 V; capacitor= 25 μF). After transfection cells are cultured in 15 ml Alpha+ medium with 10% FCS for 3 days.

The dhfr-gene located on the pXMT3 plasmid allows selection for recombinant cells in a nucleoside depleted medium. 3 days after transfection cells are placed into Alpha- medium (MEM ALPHA MEDIUM without ribonucleosides and deoxyribonucleo-sides/Gibco) containing 10% dialyzed fetal calf serum (FCSD). After 2 weeks of cultivation, recombinant cell colonies are visible. Cells are kept in Alpha- medium containing 10% FCSD for 4 additional passages before gene amplification is started.

In the presence of methotrexate (MTX), dhfr and the genes linked to it are amplified, resulting in an increased expression of the transgene. Therefore, selection for recombinant cells in a nucleoside-depleted medium is followed by cultivation in the presence of 20 nM MTX in Alpha- medium containing 10% FCSD. Further amplification is achieved by stepwise increases in methotrexate to 100 nM and 500 nM MTX.

Protein is produced by seeding pool T1/3–500 nM in Alpha- medium containing 10% FCS (GIBCO) at a density of 9×10$^3$/cm$^2$ into roller bottles. The first supernatant is collected 5 days after seeding, followed by a switch to serum free Alpha- . The second harvest is collected 3 days later, yielding a total of 1 liter supernatant for purification.

A second batch is purified from 2 liter supernatant derived from pool T1/3–500 nM adapted to serum free growth conditions. Cells are seeded at 5×10$^4$ cells/ml and the supernatant collected 6 days after seeding.

EXAMPLE 8

Purification of Fusion Protein

Figure 15:
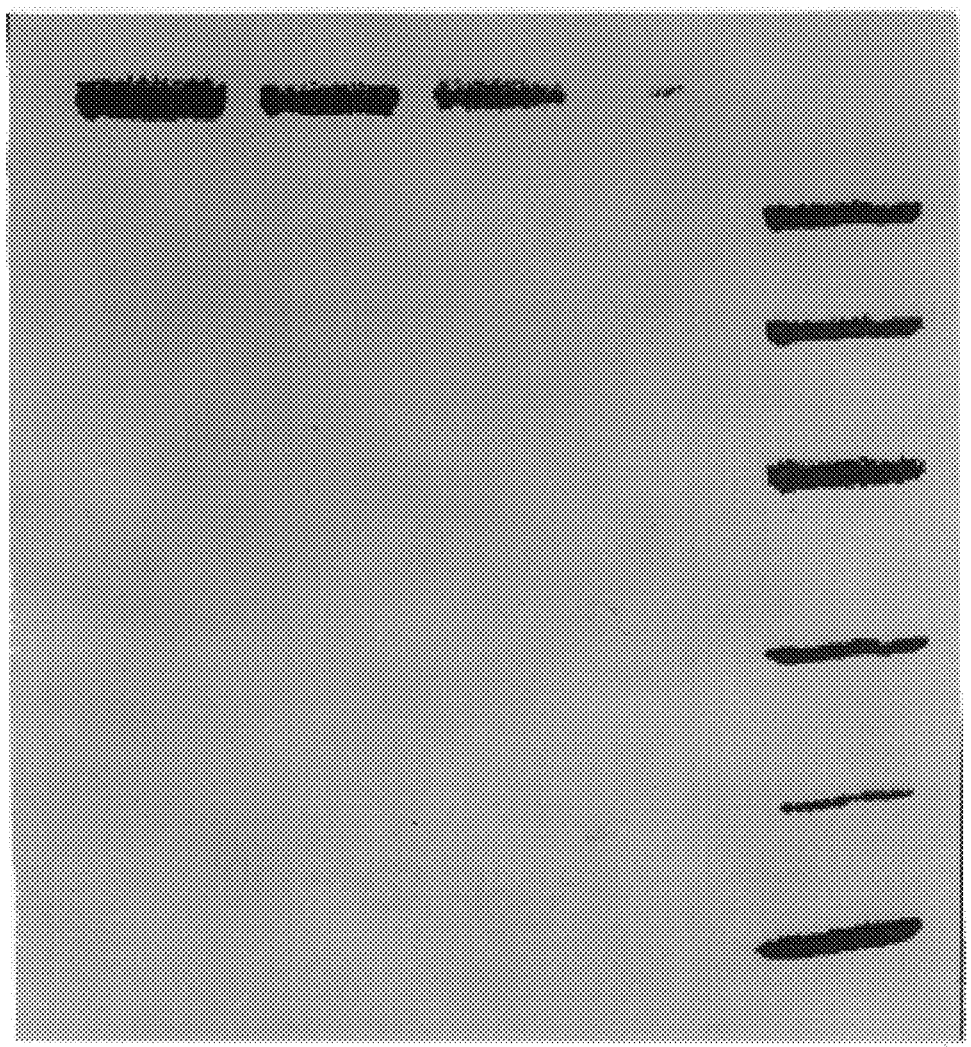

The culture supernatants from Example 7 are purified by immunoaffinity chromatography on immobilized anti-FcεRI monoclonal antibodies (e.g. 5H5-F8; mouse IgGl), produced and purified according to standard techniques:

a) Preparation of the Chromatographic Support:

The monoclonal antibodies are coupled to CNBr-activated Sepharose 4B (Pharmacia, Uppsala, Sweden) at a density of 10 mg antibodies/ml gel according to the manufacturer's instructions. Excess reactive groups are subsequently blocked with ethanolamine and the resin stored in PBS supplemented with 0.02% NaN$_3$ until use.

b) Affinity Chromatography:

Clear culture supernatant is applied to a 5 ml antibody column equilibrated in PBS at a flow rate of 0.5 ml/min. The absorbed material is eluted in 50 mM citric acid, 140 mM NaCl, pH 2.70. Protein containing fractions are immediately adjusted to pH 7.0 (NaOH) followed by sterile filtration.

c) Quantification/Characterization:

The concentration of the dimeric fusion polypeptide is determined by absorption at 280 nm in its native conformation in 30 mM (3-[N-morpholino]propane)sulfonic acid (MOPS), pH 7.0 and in the denatured form (6 M guanidine.HCl). The corresponding molar absorption coefficient is calculated from the number of tryptophan, tyrosine and cystine residues using the tabulated absorption coefficients of these amino acids in model compounds and corrected for the difference in optical density between folded and unfolded protein. The fusion protein contains 17 tryptophans, 40 tyrosines and 21 cystines, which results in a theoretical extinction coefficient of 150840 M$^{-1}$cm$^{-1}$. The quality of the purified material is assessed by standard SDS-PAGE and by N-terminus automated gas-phase Edman degradation sequencing and mass spectrometry. Upon SDS-PAGE (FIG. 15) the polypeptide migrates with an apparent molecular weight of about 140 kDa, reflecting about 28% glycosylation (theoretical MW without glycosylation: 108'863.61 Da).

What is claimed is:

1. The fusion polypeptide defined by residues $Val_{26}$-$Leu_{978}$ of SEQ ID NO. 3 or the pharmaceutically acceptable salts thereof.

2. The fusion polypeptide of claim 1.

3. A polynucleotide sequence encoding the polypeptide of claim 1.

4. The polynucleotide of sequence as set forth in SEQ. ID. NO. 4.

5. A fusion polypeptide or a pharmaceutically acceptable salt thereof comprising at least one IgE-binding domain fused to at least one human serum albumin (HSA) component, wherein the IgE-binding domain is:
   (a) the amino acid sequence defined by residues $Val_{26}$-$Leu_{204}$ of SEQ ID NO:1, or
   (b) a truncation of (a) at the carboxy terminus by 1–12 amino acids.

6. A fusion polypeptide or a pharmaceutically acceptable salt thereof of claim 5 wherein the IgE-binding domain is the amino acid sequence defined by residues $Val_{26}$-$Leu_{204}$ of SED ID NO:1.

7. A fusion polypeptide or a pharmaceutically acceptable salt thereof of claim 5 wherein:
   the HSA component is:
   (a) the amino acid sequence defined by residues $Asp25$-$Leu60[8]9$ of SEQ ID NO. 2, or
   (b) a truncation of (a) at the carboxy terminus thereof by 1–10 amino acids.

8. A polynucleotide sequence encoding the polypeptide of claim 7.

9. A fusion polypeptide or a pharmaceutically acceptable salt thereof of claim 5 wherein the HSA component is the amino acid sequence defined by residues $Asp_{25}$-$Gly_{608}$ of SEQ ID NO: 2.

10. The polynucleotide sequence encoding the polypeptide of claim 5.

11. A host cell transformed with the polynucleotide of claim 10.

12. A method of preparing the fusion polypeptide of claim 5 comprising the steps of:
   transforming a host cell with a vector comprising a polynucleotide encoding the fusion polypeptide,
   expressing the fusion polypeptide in said cell, and
   recovering the fusion polypeptide from the host cell, optionally in the form of a salt thereof.

13. A vector for expressing a polynucleotide sequence encoding a fusion polypeptide of formula I, II, III, IV or V:

I. $R_1$-L-$R_2$

II. $R_2$-L-$R_1$

III. $R_1$-L-$R_2$-L-$R_1$

IV. $R_1$-L-$R_1$-L-$R_2$

V. $R_2$-L-$R_1$-L-$R_1$ and pharmaceutically acceptable salts thereof, wherein $R_1$ is a polypeptide selected from the group consisting of a polypeptide having amino acid sequence $Val_{26}$-$Leu_{204}$ of SEQ ID NO:1 and a truncation of the amino acid sequence defined by residues $Val_{26}$-$Leu_{204}$ of SEQ ID NO:1 at the carboxy terminus by 1–12 amino acids, wherein said polypeptide binds to an IgE molecule such that IgE is inhibited from binding to its receptor, $R_2$ is a polypeptide selected from the group consisting of a polypeptide having amino acid sequence $Asp_{25}$-$Leu_{609}$ of SEQ ID NO:2 and a truncation of the amino acid sequence defined by residues $Asp_{25}$-$Leu_{609}g$ of SEQ ID NO:2 at the carboxy terminus thereof by 1–10 amino acids; and L is independently a chemical bond, wherein the vector is PXMT3-Rla-HSA-Rla.

* * * * *

UNITED STATES PATENT AND TRADEMARK OFFICE
CERTIFICATE OF CORRECTION

PATENT NO.    : 6,423,512 B1  Page 1 of 1
DATED         : July 23, 2002
INVENTOR(S)   : Mary Ellen Digan et al.

It is certified that error appears in the above-identified patent and that said Letters Patent is hereby corrected as shown below:

<u>Column 54,</u>
Line 50, should read:
-- acid sequence defined by residues $Asp_{25}$-$Leu_{609}$ of --.
Line 55, should read:
-- pXMT3. --.

Signed and Sealed this

First Day of April, 2003

JAMES E. ROGAN
*Director of the United States Patent and Trademark Office*

SEQUENCE LISTING

<160> NUMBER OF SEQ ID NOS: 38

<210> SEQ ID NO 1
<211> LENGTH: 257
<212> TYPE: PRT
<213> ORGANISM: Homo Sapiens

<400> SEQUENCE: 1

```
Met Ala Pro Ala Met Glu Ser Pro Thr Leu Leu Cys Val Ala Leu Leu
 1               5                  10                  15

Phe Phe Ala Pro Asp Gly Val Leu Ala Val Pro Gln Lys Pro Lys Val
            20                  25                  30

Ser Leu Asn Pro Pro Trp Asn Arg Ile Phe Lys Gly Glu Asn Val Thr
        35                  40                  45

Leu Thr Cys Asn Gly Asn Asn Phe Phe Glu Val Ser Ser Thr Lys Trp
```

```
            50                 55                 60
Phe His Asn Gly Ser Leu Ser Glu Glu Thr Asn Ser Ser Leu Asn Ile
65                  70                  75                  80

Val Asn Ala Lys Phe Glu Asp Ser Gly Glu Tyr Lys Cys Gln His Gln
                85                  90                  95

Gln Val Asn Glu Ser Glu Pro Val Tyr Leu Glu Val Phe Ser Asp Trp
            100                 105                 110

Leu Leu Leu Gln Ala Ser Ala Glu Val Val Met Glu Gly Gln Pro Leu
            115                 120                 125

Phe Leu Arg Cys His Gly Trp Arg Asn Trp Asp Val Tyr Lys Val Ile
            130                 135                 140

Tyr Tyr Lys Asp Gly Glu Ala Leu Lys Tyr Trp Tyr Glu Asn His Asn
145                 150                 155                 160

Ile Ser Ile Thr Asn Ala Thr Val Glu Asp Ser Gly Thr Tyr Tyr Cys
                165                 170                 175

Thr Gly Lys Val Trp Gln Leu Asp Tyr Glu Ser Glu Pro Leu Asn Ile
                180                 185                 190

Thr Val Ile Lys Ala Pro Arg Glu Lys Tyr Trp Leu Gln Phe Phe Ile
            195                 200                 205

Pro Leu Leu Val Val Ile Leu Phe Ala Val Asp Thr Gly Leu Phe Ile
            210                 215                 220

Ser Thr Gln Gln Gln Val Thr Phe Leu Leu Lys Ile Lys Arg Thr Arg
225                 230                 235                 240

Lys Gly Phe Arg Leu Leu Asn Pro His Pro Lys Pro Asn Pro Lys Asn
                245                 250                 255

Asn

<210> SEQ ID NO 2
<211> LENGTH: 609
<212> TYPE: PRT
<213> ORGANISM: Homo Sapiens

<400> SEQUENCE: 2

Met Lys Trp Val Thr Phe Ile Ser Leu Leu Phe Leu Phe Ser Ser Ala
 1                   5                  10                  15

Tyr Ser Arg Gly Val Phe Arg Arg Asp Ala His Lys Ser Glu Val Ala
                20                  25                  30

His Arg Phe Lys Asp Leu Gly Glu Glu Asn Phe Lys Ala Leu Val Leu
            35                  40                  45

Ile Ala Phe Ala Gln Tyr Leu Gln Gln Cys Pro Phe Glu Asp His Val
        50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
```

-continued

```
                165                 170                 175
Glu Leu Leu Phe Phe Ala Lys Arg Tyr Lys Ala Ala Phe Thr Glu Cys
            180                 185                 190
Cys Gln Ala Ala Asp Lys Ala Ala Cys Leu Leu Pro Lys Leu Asp Glu
            195                 200             205
Leu Arg Asp Glu Gly Lys Ala Ser Ser Ala Lys Gln Arg Leu Lys Cys
        210                 215                 220
Ala Ser Leu Gln Lys Phe Gly Glu Arg Ala Phe Lys Ala Trp Ala Val
225                 230                 235                 240
Ala Arg Leu Ser Gln Arg Phe Pro Lys Ala Glu Phe Ala Glu Val Ser
                245                 250                 255
Lys Leu Val Thr Asp Leu Thr Lys Val His Thr Glu Cys Cys His Gly
            260                 265                 270
Asp Leu Leu Glu Cys Ala Asp Asp Arg Ala Asp Leu Ala Lys Tyr Ile
            275                 280             285
Cys Glu Asn Gln Asp Ser Ile Ser Ser Lys Leu Lys Glu Cys Cys Glu
        290                 295                 300
Lys Pro Leu Leu Glu Lys Ser His Cys Ile Ala Glu Val Glu Asn Asp
305                 310                 315                 320
Glu Met Pro Ala Asp Leu Pro Ser Leu Ala Ala Asp Phe Val Glu Ser
                325                 330                 335
Lys Asp Val Cys Lys Asn Tyr Ala Glu Ala Lys Asp Val Phe Leu Gly
            340                 345                 350
Met Phe Leu Tyr Glu Tyr Ala Arg Arg His Pro Asp Tyr Ser Val Val
            355                 360             365
Leu Leu Leu Arg Leu Ala Lys Thr Tyr Glu Thr Thr Leu Glu Lys Cys
        370                 375                 380
Cys Ala Ala Ala Asp Pro His Glu Cys Tyr Ala Lys Val Phe Asp Glu
385                 390                 395                 400
Phe Lys Pro Leu Val Glu Glu Pro Gln Asn Leu Ile Lys Gln Asn Cys
                405                 410                 415
Glu Leu Phe Lys Gln Leu Gly Glu Tyr Lys Phe Gln Asn Ala Leu Leu
            420                 425                 430
Val Arg Tyr Thr Lys Lys Val Pro Gln Val Ser Thr Pro Thr Leu Val
            435                 440             445
Glu Val Ser Arg Asn Leu Gly Lys Val Gly Ser Lys Cys Cys Lys His
        450                 455                 460
Pro Glu Ala Lys Arg Met Pro Cys Ala Glu Asp Tyr Leu Ser Val Val
465                 470                 475                 480
Leu Asn Gln Leu Cys Val Leu His Glu Lys Thr Pro Val Ser Asp Arg
                485                 490                 495
Val Thr Lys Cys Cys Thr Glu Ser Leu Val Asn Arg Arg Pro Cys Phe
            500                 505                 510
Ser Ala Leu Glu Val Asp Glu Thr Tyr Val Pro Lys Glu Phe Asn Ala
            515                 520             525
Glu Thr Phe Thr Phe His Ala Asp Ile Cys Thr Leu Ser Glu Lys Glu
        530                 535                 540
Arg Gln Ile Lys Lys Gln Thr Ala Leu Val Glu Leu Val Lys His Lys
545                 550                 555                 560
Pro Lys Ala Thr Lys Glu Gln Leu Lys Ala Val Met Asp Asp Phe Ala
                565                 570                 575
Ala Phe Val Glu Lys Cys Cys Lys Ala Asp Asp Lys Glu Thr Cys Phe
            580                 585                 590
```

Ala Glu Glu Gly Lys Lys Leu Val Ala Ala Ser Gln Ala Ala Leu Gly
            595                 600                 605

Leu

<210> SEQ ID NO 3
<211> LENGTH: 978
<212> TYPE: PRT
<213> ORGANISM: Artificial Sequence
<220> FEATURE:
<223> OTHER INFORMATION: Fusion polypeptide

<400> SEQUENCE: 3

Met Ala Pro Ala Met Glu Ser Pro Thr Leu Leu Cys Val Ala Leu Leu
 1               5                  10                  15

Phe Phe Ala Pro Asp Gly Val Leu Ala Val Pro Gln Lys Pro Lys Val
            20                  25                  30

Ser Leu Asn Pro Pro Trp Asn Arg Ile Phe Lys Gly Glu Asn Val Thr
        35                  40                  45

Leu Thr Cys Asn Gly Asn Asn Phe Phe Glu Val Ser Ser Thr Lys Trp
    50                  55                  60

Phe His Asn Gly Ser Leu Ser Glu Glu Thr Asn Ser Ser Leu Asn Ile
65                  70                  75                  80

Val Asn Ala Lys Phe Glu Asp Ser Gly Glu Tyr Lys Cys Gln His Gln
                85                  90                  95

Gln Val Asn Glu Ser Glu Pro Val Tyr Leu Glu Val Phe Ser Asp Trp
            100                 105                 110

Leu Leu Leu Gln Ala Ser Ala Glu Val Val Met Glu Gly Gln Pro Leu
        115                 120                 125

Phe Leu Arg Cys His Gly Trp Arg Asn Trp Asp Val Tyr Lys Val Ile
    130                 135                 140

Tyr Tyr Lys Asp Gly Glu Ala Leu Lys Tyr Trp Tyr Glu Asn His Asn
145                 150                 155                 160

Ile Ser Ile Thr Asn Ala Thr Val Glu Asp Ser Gly Thr Tyr Tyr Cys
                165                 170                 175

Thr Gly Lys Val Trp Gln Leu Asp Tyr Glu Ser Glu Pro Leu Asn Ile
            180                 185                 190

Thr Val Ile Lys Ala Pro Arg Glu Lys Tyr Trp Leu Ala Ser Gly Gly
        195                 200                 205

Gly Gly Ser Asp Ala His Lys Ser Glu Val Ala His Arg Phe Lys Asp
    210                 215                 220

Leu Gly Glu Glu Asn Phe Lys Ala Leu Val Leu Ile Ala Phe Ala Gln
225                 230                 235                 240

Tyr Leu Gln Gln Cys Pro Phe Glu Asp His Val Lys Leu Val Asn Glu
                245                 250                 255

Val Thr Glu Phe Ala Lys Thr Cys Val Ala Asp Glu Ser Ala Glu Asn
            260                 265                 270

Cys Asp Lys Ser Leu His Thr Leu Phe Gly Asp Lys Leu Cys Thr Val
        275                 280                 285

Ala Thr Leu Arg Glu Thr Tyr Gly Glu Met Ala Asp Cys Cys Ala Lys
    290                 295                 300

Gln Glu Pro Glu Arg Asn Glu Cys Phe Leu Gln His Lys Asp Asp Asn
305                 310                 315                 320

Pro Asn Leu Pro Arg Leu Val Arg Pro Glu Val Asp Val Met Cys Thr
                325                 330                 335

-continued

```
Ala Phe His Asp Asn Glu Glu Thr Phe Leu Lys Lys Tyr Leu Tyr Glu
            340                 345                 350

Ile Ala Arg Arg His Pro Tyr Phe Tyr Ala Pro Glu Leu Leu Phe Phe
            355                 360                 365

Ala Lys Arg Tyr Lys Ala Ala Phe Thr Glu Cys Cys Gln Ala Ala Asp
            370                 375                 380

Lys Ala Ala Cys Leu Leu Pro Lys Leu Asp Glu Leu Arg Asp Glu Gly
385                 390                 395                 400

Lys Ala Ser Ser Ala Lys Gln Arg Leu Lys Cys Ala Ser Leu Gln Lys
                405                 410                 415

Phe Gly Glu Arg Ala Phe Lys Ala Trp Ala Val Ala Arg Leu Ser Gln
            420                 425                 430

Arg Phe Pro Lys Ala Glu Phe Ala Glu Val Ser Lys Leu Val Thr Asp
            435                 440                 445

Leu Thr Lys Val His Thr Glu Cys Cys His Gly Asp Leu Leu Glu Cys
            450                 455                 460

Ala Asp Asp Arg Ala Asp Leu Ala Lys Tyr Ile Cys Glu Asn Gln Asp
465                 470                 475                 480

Ser Ile Ser Ser Lys Leu Lys Glu Cys Cys Glu Lys Pro Leu Leu Glu
                485                 490                 495

Lys Ser His Cys Ile Ala Glu Val Glu Asn Asp Glu Met Pro Ala Asp
            500                 505                 510

Leu Pro Ser Leu Ala Ala Asp Phe Val Glu Ser Lys Asp Val Cys Lys
            515                 520                 525

Asn Tyr Ala Glu Ala Lys Asp Val Phe Leu Gly Met Phe Leu Tyr Glu
            530                 535                 540

Tyr Ala Arg Arg His Pro Asp Tyr Ser Val Val Leu Leu Leu Arg Leu
545                 550                 555                 560

Ala Lys Thr Tyr Glu Thr Thr Leu Glu Lys Cys Cys Ala Ala Ala Asp
            565                 570                 575

Pro His Glu Cys Tyr Ala Lys Val Phe Asp Glu Phe Lys Pro Leu Val
            580                 585                 590

Glu Glu Pro Gln Asn Leu Ile Lys Gln Asn Cys Glu Leu Phe Lys Gln
            595                 600                 605

Leu Gly Glu Tyr Lys Phe Gln Asn Ala Leu Leu Val Arg Tyr Thr Lys
            610                 615                 620

Lys Val Pro Gln Val Ser Thr Pro Thr Leu Val Glu Val Ser Arg Asn
625                 630                 635                 640

Leu Gly Lys Val Gly Ser Lys Cys Cys Lys His Pro Glu Ala Lys Arg
                645                 650                 655

Met Pro Cys Ala Glu Asp Tyr Leu Ser Val Val Leu Asn Gln Leu Cys
            660                 665                 670

Val Leu His Glu Lys Thr Pro Val Ser Asp Arg Val Thr Lys Cys Cys
            675                 680                 685

Thr Glu Ser Leu Val Asn Arg Arg Pro Cys Phe Ser Ala Leu Glu Val
            690                 695                 700

Asp Glu Thr Tyr Val Pro Lys Glu Phe Asn Ala Glu Thr Phe Thr Phe
705                 710                 715                 720

His Ala Asp Ile Cys Thr Leu Ser Glu Lys Glu Arg Gln Ile Lys Lys
                725                 730                 735

Gln Thr Ala Leu Val Glu Leu Val Lys His Lys Pro Lys Ala Thr Lys
            740                 745                 750

Glu Gln Leu Lys Ala Val Met Asp Asp Phe Ala Ala Phe Val Glu Lys
```

```
            755                 760                 765
Cys Cys Lys Ala Asp Asp Lys Glu Thr Cys Phe Ala Glu Glu Gly Lys
        770                 775                 780

Lys Leu Val Ala Ala Ser Gln Ala Ala Leu Gly Gly Gly Gly Ser Val
785                 790                 795                 800

Pro Gln Lys Pro Lys Val Ser Leu Asn Pro Pro Trp Asn Arg Ile Phe
                805                 810                 815

Lys Gly Glu Asn Val Thr Leu Thr Cys Asn Gly Asn Asn Phe Phe Glu
            820                 825                 830

Val Ser Ser Thr Lys Trp Phe His Asn Gly Ser Leu Ser Glu Glu Thr
        835                 840                 845

Asn Ser Ser Leu Asn Ile Val Asn Ala Lys Phe Glu Asp Ser Gly Glu
850                 855                 860

Tyr Lys Cys Gln His Gln Gln Val Asn Glu Ser Glu Pro Val Tyr Leu
865                 870                 875                 880

Glu Val Phe Ser Asp Trp Leu Leu Leu Gln Ala Ser Ala Glu Val Val
                885                 890                 895

Met Glu Gly Gln Pro Leu Phe Leu Arg Cys His Gly Trp Arg Asn Trp
            900                 905                 910

Asp Val Tyr Lys Val Ile Tyr Tyr Lys Asp Gly Glu Ala Leu Lys Tyr
            915                 920                 925

Trp Tyr Glu Asn His Asn Ile Ser Ile Thr Asn Ala Thr Val Glu Asp
        930                 935                 940

Ser Gly Thr Tyr Tyr Cys Thr Gly Lys Val Trp Gln Leu Asp Tyr Glu
945                 950                 955                 960

Ser Glu Pro Leu Asn Ile Thr Val Ile Lys Ala Pro Arg Glu Lys Tyr
                965                 970                 975

Trp Leu

<210> SEQ ID NO 4
<211> LENGTH: 2955
<212> TYPE: DNA
<213> ORGANISM: Artificial Sequence
<220> FEATURE:
<223> OTHER INFORMATION: Fusion polynucleotide

<400> SEQUENCE: 4
gaattcacca tggctcctgc catggaatcc cctactctac tgtgtgtagc cttactgttc      60
ttcgctccag atggcgtgtt agcagtccct cagaaaccta aggtctcctt gaaccctcca     120
tggaatagaa tatttaaagg agagaatgtg actcttacat gtaatgggaa caatttctttt    180
gaagtcagtt ccaccaaatg gttccacaat ggcagccttt cagaagagac aaattcaagt    240
ttgaatattg tgaatgccaa atttgaagac agtggagaat acaaatgtca gcaccaacaa    300
gttaatgaga gtgaacctgt gtacctggaa gtcttcagtg actggctgct ccttcaggcc    360
tctgctgagg tggtgatgga gggccagccc ctcttcctca ggtgccatgg ttggaggaac    420
tgggatgtgt acaaggtgat ctattataag gatggtgaag ctctcaagta ctggtatgag    480
aaccacaaca tctccattac aaatgccaca gttgaagaca gtggaaccta ctactgtacg    540
ggcaaagtgt ggcagctgga ctatgagtct gagcccctca acattactgt aataaaagct    600
ccgcgtgaga agtactggct tgctagcgtt ggaggtggat ccgatgcaca caagagtgag    660
gttgctcatc ggtttaaaga tttgggagaa gaaaatttca agccttggt gttgattgcc    720
tttgctcagt atcttcagca gtgtccattt gaagatcatg taaaattagt gaatgaagta    780
```

```
actgaatttg caaaaacatg tgttgctgat gagtcagctg aaaattgtga caaatcactt      840
catacccttt ttggagacaa attatgcaca gttgcaactc ttcgtgaaac ctatggtgaa      900
atggctgact gctgtgcaaa acaagaacct gagagaaatg aatgcttctt gcaacacaaa      960
gatgacaacc caaacctccc ccgattggtg agaccagagg ttgatgtgat gtgcactgct     1020
tttcatgaca atgaagagac atttttgaaa aaatacttat atgaaattgc cagaagacat     1080
ccttactttt atgccccgga actccttttc tttgctaaaa ggtataaagc tgcttttaca     1140
gaatgttgcc aagctgctga taaagctgcc tgcctgttgc caaagctcga tgaacttcgg     1200
gatgaaggga aggcttcgtc tgccaaacag agactcaagt gtgccagtct ccaaaaattt     1260
ggagaaagag ctttcaaagc atgggcagta gctcgcctga ccagagatt tcccaaagct     1320 gagtttgcag aagtttccaa gttagtgaca gatcttacca aagtccacac ggaatgctgc     1380
catggagatc tgcttgaatg tgctgatgac agggcggacc ttgccaagta tatctgtgaa     1440
aatcaagatt cgatctccag taaactgaag gaatgctgtg aaaaacctct gttggaaaaa     1500
tcccactgca ttgccgaagt ggaaaatgat gagatgcctg ctgacttgcc ttcattagct     1560
gctgattttg ttgaaagtaa ggatgtttgc aaaaactatg ctgaggcaaa ggatgtcttc     1620
ctgggcatgt ttttgtatga atatgcaaga aggcatcctg attactctgt cgtgctgctg     1680
ctgagacttg ccaagacata tgaaaccact ctagagaagt gctgtgccgc tgcagatcct     1740
catgaatgct atgccaaagt gttcgatgaa tttaaacctc ttgtggaaga gcctcagaat     1800
ttaatcaaac aaaattgtga gcttttttaag cagcttggag agtacaaatt ccagaatgcg     1860
ctattagttc gttacaccaa gaaagtaccc caagtgtcaa ctccaactct tgtagaggtc     1920
tcaagaaacc taggaaaagt gggcagcaaa tgttgtaaac atcctgaagc aaaaagaatg     1980
ccctgtgcag aagactatct atccgtggtc ctgaaccagt tatgtgtgtt gcatgagaaa     2040
acgccagtaa gtgacagagt caccaaatgc tgcacagaat ccttggtgaa caggcgacca     2100
tgcttttcag ctctggaagt cgatgaaaca tacgttccca aagagtttaa tgctgaaaca     2160
ttcaccttcc atgcagatat atgcacactt tctgagaagg agacaaat caagaaacaa     2220 actgcacttg ttgagcttgt gaaacacaag cccaaggcaa caaaagagca actgaaagct     2280
gttatggatg atttcgcagc ttttgtagag aagtgctgca aggctgacga taaggagacc     2340
tgctttgccg aggagggtaa aaaacttgtt gctgcaagtc aagctgcctt aggtggaggt     2400
ggatccgtcc ctcagaaacc taaggtctcc ttgaaccctc catggaatag aatatttaaa     2460
ggagagaatg tgactcttac atgtaatggg aacaatttct ttgaagtcag ttccaccaaa     2520
tggttccaca atggcagcct ttcagaagag acaaattcaa gtttgaatat tgtgaatgcc     2580
aaatttgaag acagtggaga atacaaatgt cagcaccaac aagttaatga gagtgaacct     2640
gtgtacctgg aagtcttcag tgactggctg ctccttcagg cctctgctga ggtggtgatg     2700
gagggccagc ccctcttcct caggtgccat ggttggagga actgggatgt gtacaaggtg     2760
atctattata aggatggtga agctctcaag tactggtatg agaaccacaa catctccatt     2820
acaaatgcca cagttgaaga cagtggaacc tactactgta cgggcaaagt gtggcagctg     2880
gactatgagt ctgagcccct caacattact gtaataaaag ctccgcgtga aagtactgg     2940 ctatagtaag aattc                                                      2955

<210> SEQ ID NO 5
<211> LENGTH: 1827
<212> TYPE: DNA
<213> ORGANISM: Artificial Sequence
```

<220> FEATURE:
<223> OTHER INFORMATION: Fusion Polynucleotide

<400> SEQUENCE: 5

```
atgaagtggg taacctttat ttcccttctt tttctcttta gctcggctta ttccaggggt    60
gtgtttcgtc gagatgcaca caagagtgag gttgctcatc ggtttaaaga tttgggagaa   120
gaaaatttca aagccttggt gttgattgcc tttgctcagt atcttcagca gtgtccattt   180
gaagatcatg taaaattagt gaatgaagta actgaatttg caaaaacatg tgtagctgat   240
gagtcagctg aaaattgtga caaatcactt catacccttt tgggagacaa attatgcaca   300
gttgcaactc ttcgtgaaac ctatggtgaa atggctgact gctgtgcaaa acaagaacct   360
gagagaaatg aatgcttctt gcaacacaaa gatgacaacc caaacctccc ccgattggtg   420
agaccagagg ttgatgtgat gtgcactgct tttcatgaca tgaagagac attttttgaaa   480
aaatacttat atgaaattgc cagaagacat ccttacttt atgccccgga actccttttc   540
tttgctaaaa ggtataaagc tgcttttaca gaatgttgcc aagctgctga taaagctgcc   600
tgcctgttgc aaagctcga tgaacttcgg atgaaggga aggcttcgtc tgccaaacag   660
agactcaaat gtgccagtct ccaaaaattt ggagaaagag ctttcaaagc atgggcagtg   720
gctcgcctga gccagagatt tcccaaagct gagtttgcag aagtttccaa gttagtgaca   780
gatcttacca agtccacac ggaatgctgc catggagatc tgcttgaatg tgctgatgac   840
agggcggacc ttgccaagta tatctgtgaa atcaggatt cgatctccag taaactgaag   900
gaatgctgtg aaaaacctct gttggaaaaa tcccactgca ttgccgaagt ggaaaatgat   960
gagatgcctg ctgacttgcc ttcattagct gctgattttg ttgaaagtaa ggatgtttgc  1020
aaaaactatg ctgaggcaaa ggatgtcttc ctgggcatgt ttttgtatga atatgcaaga  1080
aggcatcctg attactctgt cgtgctgctg ctgagacttg ccaagacata tgaaaccact  1140
ctagagaagt gctgtgccgc tgcagatcct catgaatgct atgccaaagt gttcgatgaa  1200
tttaaacctc ttgtggaaga gcctcagaat ttaatcaaac aaaactgtga gcttttaag   1260
cagcttggag agtacaaatt ccagaatgcg ctattagttc gttacaccaa gaaagtaccc  1320
caagtgtcaa ctccaactct tgtagaggtc tcaagaaacc taggaaaagt gggcagcaaa  1380
tgttgtaaac atcctgaagc aaaaagaatg ccctgtgcag aagactatct atccgtggtc  1440
ctgaaccagt tatgtgtgtt gcatgagaaa acgccagtaa gtgacagagt cacaaaatgc  1500
tgcacagagt ccttggtgaa caggcgacca tgcttttcag ctctggaagt cgatgaaaca  1560
tacgttccca agagtttaa tgctgaaaca ttcaccttcc atgcagatat atgcacactt  1620
tctgagaagg agagacaaat caagaaacaa actgcacttg ttgagcttgt gaacacaag  1680
cccaaggcaa caaagagca actgaaagct gttatggatg atttcgcagc ttttgtagag  1740
aagtgctgca aggctgacga taaggagacc tgctttgccg aggagggtaa aaaacttgtt  1800
gctgcaagtc aagctgcctt aggctta                                     1827
```

<210> SEQ ID NO 6
<211> LENGTH: 773
<212> TYPE: DNA
<213> ORGANISM: Artificial Sequence
<220> FEATURE:
<223> OTHER INFORMATION: Fusion Polynucleotide

<400> SEQUENCE: 6

```
atggctcctg ccatggaatc ccctactcta ctgtgtgtag ccttactgtt cttcgctcca    60
```

-continued

| | | |
|---|---|---|
| gatggcgtgt tagcagtccc tcagaaacct aaggtctcct tgaaccctcc atggaataga | 120 |
| atatttaaag gagagaatgt gactcttaca tgtaatggga acaatttctt tgaagtcagt | 180 |
| tccaccaaat ggttccacaa tggcagcctt tcagaagaga caaattcaag tttgaatatt | 240 |
| gtgaatgcca aatttgaaga cagtggagaa tacaaatgtc agcaccaaca agttaatgag | 300 |
| agtgaacctg tgtacctgga agtcttcagt gactggctgc tccttcaggc tctgctgag | 360 |
| gtggtgatgg agggccagcc cctcttcctc aggtgccatg gttggaggaa ctgggatgtg | 420 |
| tacaaggtga tctattataa ggatggtgaa gctctcaagt actggtatga gaaccacaac | 480 |
| atctccatta caaatgccac agttgaagac agtggaacct actactgtac gggcaaagtg | 540 |
| tggcagctgg actatgagtc tgagcccctc aacattactg taataaaagc tccgcgtgag | 600 |
| aagtactggc tacaattttt tatcccattg ttggtggtga ttctgtttgc tgtggacaca | 660 |
| ggattattta tctcaactca gcagcaggtc acatttctct tgaagattaa gagaaccagg | 720 |
| aaaggcttca gacttctgaa cccacatcct aagccaaacc ccaaaaacaa ctg | 773 |

<210> SEQ ID NO 7
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 7
tcaaagcctt ggtgttgatt g                                                 21

<210> SEQ ID NO 8
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 8
tgaaatggct gactgctgtg                                                   20

<210> SEQ ID NO 9
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 9
aggtataaag ctgcttttac ag                                                22

<210> SEQ ID NO 10
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 10
tgagccagag atttcccaaa g                                                 21

<210> SEQ ID NO 11
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 11
tcccactgca ttgccgaagt g                                              21

<210> SEQ ID NO 12
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 12
ctagagaagt gctgtgccgc t                                              21

<210> SEQ ID NO 13
<211> LENGTH: 19
<212> TYPE: DNA
<213> ORGANISM: Artificial Sequence
<220> FEATURE:
<223> OTHER INFORMATION: Oligonucleotide Primer

<400> SEQUENCE: 13
tgtcaactcc aactcttgt                                                 19

<210> SEQ ID NO 14
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 14
cagctctgga agtcgatgaa a                                              21

<210> SEQ ID NO 15
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 15
ctttgaaagc tctttctcca                                                20

<210> SEQ ID NO 16
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 16
attctggaat ttgtactctc c                                              21

<210> SEQ ID NO 17
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 17
acactgctga agatactgag c                                              21

<210> SEQ ID NO 18

```
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 18
tctggcaatt tcatataagt a                                            21

<210> SEQ ID NO 19
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 19
atgttgtaaa catcctgaag c                                            21

<210> SEQ ID NO 20
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 20
acctgctttg ccgaggaggg t                                            21

<210> SEQ ID NO 21
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 21
acaagagtga ggttgctcat c                                            21

<210> SEQ ID NO 22
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 22
cctttaaata ttctattcca t                                            21

<210> SEQ ID NO 23
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 23
gaagtcagtt ccaccaaatg gt                                           22

<210> SEQ ID NO 24
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 24
```

```
gatggagggc cagcccctct t                                              21

<210> SEQ ID NO 25
<211> LENGTH: 25
<212> TYPE: DNA
<213> ORGANISM: Artificial Sequence
<220> FEATURE:
<223> OTHER INFORMATION: Oligonucleotide Primer

<400> SEQUENCE: 25
tgtgagcttt ttaagcagct tggag                                          25

<210> SEQ ID NO 26
<211> LENGTH: 25
<212> TYPE: DNA
<213> ORGANISM: Artificial Sequence
<220> FEATURE:
<223> OTHER INFORMATION: Oligonucleotide Primer

<400> SEQUENCE: 26
ctccaagctg cttaaaaagc tcaca                                          25

<210> SEQ ID NO 27
<211> LENGTH: 40
<212> TYPE: DNA
<213> ORGANISM: Artificial Sequence
<220> FEATURE:
<223> OTHER INFORMATION: Oligonucleotide Primer

<400> SEQUENCE: 27
tcatggatcc gtccctcaga aacctaaggt ctccttgaac                          40

<210> SEQ ID NO 28
<211> LENGTH: 52
<212> TYPE: DNA
<213> ORGANISM: Artificial Sequence
<220> FEATURE:
<223> OTHER INFORMATION: Oligonucleotide Primer

<400> SEQUENCE: 28
tcatgtcgac gaattcttac tatagccagt acttctcacg cggagctttt at            52

<210> SEQ ID NO 29
<211> LENGTH: 49
<212> TYPE: DNA
<213> ORGANISM: Artificial Sequence
<220> FEATURE:
<223> OTHER INFORMATION: Oligonucleotide Primer

<400> SEQUENCE: 29
tcatgagctc gaattcacca tggctcctgc catggaatcc cctactcta               49

<210> SEQ ID NO 30
<211> LENGTH: 49
<212> TYPE: DNA
<213> ORGANISM: Artificial Sequence
<220> FEATURE:
<223> OTHER INFORMATION: Oligonucleotide Primer

<400> SEQUENCE: 30
tcatactagt gaattcacca tgaagtgggt aacctttatt tcccttctt                49

<210> SEQ ID NO 31
<211> LENGTH: 49
<212> TYPE: DNA
```

-continued

<213> ORGANISM: Artificial Sequence
<220> FEATURE:
<223> OTHER INFORMATION: Oligonucleotide Primer

<400> SEQUENCE: 31
tcataagctt gaattcctat tataagccta aggcagcttg acttgcagc        49

<210> SEQ ID NO 32
<211> LENGTH: 62
<212> TYPE: DNA
<213> ORGANISM: Artificial Sequence
<220> FEATURE:
<223> OTHER INFORMATION: Oligonucleotide Primer

<400> SEQUENCE: 32
gcggccgcgc tagcggtgga ggtggatccg atgcacacaa gagtgaggtt gctcatcggt        60
tt        62

<210> SEQ ID NO 33
<211> LENGTH: 37
<212> TYPE: DNA
<213> ORGANISM: Artificial Sequence
<220> FEATURE:
<223> OTHER INFORMATION: Oligonucleotide Primer

<400> SEQUENCE: 33
tcatccatgg cagcattccg tgtggacttt ggtaaga        37

<210> SEQ ID NO 34
<211> LENGTH: 19
<212> TYPE: DNA
<213> ORGANISM: Artificial Sequence
<220> FEATURE:
<223> OTHER INFORMATION: Oligonucleotide Primer

<400> SEQUENCE: 34
ttaggtggag gtggatcca        19

<210> SEQ ID NO 35
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 35
agcttggatc cacctccacc        20

<210> SEQ ID NO 36
<211> LENGTH: 46
<212> TYPE: DNA
<213> ORGANISM: Artificial Sequence
<220> FEATURE:
<223> OTHER INFORMATION: Oligonucleotide Primer

<400> SEQUENCE: 36
tcatgcggcc gcgctagcaa gccagtactt ctcacgcgga gctttt        46

<210> SEQ ID NO 37
<211> LENGTH: 4
<212> TYPE: PRT
<213> ORGANISM: Artificial Sequence
<220> FEATURE:
<223> OTHER INFORMATION: Linker

<400> SEQUENCE: 37

```
-continued

Gly Gly Gly Ser
 1

<210> SEQ ID NO 38
<211> LENGTH: 7
<212> TYPE: PRT
<213> ORGANISM: Artificial Sequence
<220> FEATURE:
<223> OTHER INFORMATION: Linker

<400> SEQUENCE: 38

Ala Ser Gly Gly Gly Gly Ser
 1               5
```